US006737407B1

(12) United States Patent
Ng et al.

(10) Patent No.: US 6,737,407 B1
(45) Date of Patent: May 18, 2004

(54) TREATMENT OF OBESITY

(75) Inventors: Frank Man-Woon Ng, Kew (AU); Woel-Jia Jiang, Clayton (AU)

(73) Assignee: Metabolic Pharmaceuticals, Ltd., Toorak (AU)

( * ) Notice: Subject to any disclaimer, the term of this patent is extended or adjusted under 35 U.S.C. 154(b) by 0 days.

(21) Appl. No.: 09/508,054

(22) PCT Filed: Sep. 4, 1998

(86) PCT No.: PCT/AU98/00724

§ 371 (c)(1),
(2), (4) Date: Apr. 20, 2000

(87) PCT Pub. No.: WO99/12969

PCT Pub. Date: Mar. 18, 1999

(30) Foreign Application Priority Data

Sep. 8, 1997 (AU) .............................................. PO9001
Nov. 13, 1997 (AU) .............................................. PP0398

(51) Int. Cl.$^7$ ........................ A61K 38/16; A61K 38/19; A61K 38/18; C07K 14/485; C07K 14/52
(52) U.S. Cl. .............................. 514/13; 514/2; 514/12; 530/300; 530/326
(58) Field of Search ................................ 530/300, 326; 514/2, 12, 13

(56) References Cited

U.S. PATENT DOCUMENTS

| 4,863,901 A | 9/1989 | Wilmore |
| 4,871,835 A | 10/1989 | Aviv et al. |
| 5,597,797 A | 1/1997 | Clark |

FOREIGN PATENT DOCUMENTS

AU          77727/94          5/1996

OTHER PUBLICATIONS

Nicoll et al. Endocrine Reviews. 7(2): 169–203, 1986.*
Natera et al.; "Reduction of Cumulative Body Weight Gain and Adipose Tissue Mass in Obese Mice: Response to Chronic Treatment with Synthetic HGH 177–191 Peptide"; Biochemistry and Molecular Biology International; vol. 33, No. 5; Aug. 1994; pp. 1011–1021.
Wu et al.; "Antilipogenic Action of Synthetic C–Terminal Sequence 177–191 of Human Growth Hormone"; Biochemistry and Molecular Biology International; vol. 30, No. 1; May 1993; pp. 187–196.
Wade et al.; "Effect of C–Terminal Chain Shortening on the Insulin–antagonistic Activity on Human Growth Hormone 177–191"; Acta Endocrinologica; vol. 101; Sep.–Dec. 1983; pp. 10–14.

Ma et al.; "The Mechanism of the Hyperglycaemic Action of Synthetic Peptides Related to the C–Terminal Sequence of Human Growth Hormone"; Biochemical et Biophysical Acta; vol. 716; 1982; pp. 400–409.
Wade et al.; "Diabetogenic Action of Human Growth Hormone"; Int. Journal. Peptide and Protein Research; vol. 13, No. 2; 1979; pp. 195–200.
Weerasinghe et al.; "Effect of Synthetic C–Terminal Fragments of hGH on Glucose Oxidation by Isolated Islets"; vol. 236; Jan.–Jun. 1979; pp. 4–9.
Newman et al.; "Effects of Part Sequence of Human Growth Hormone on in Vivo Hepatic Glycogen Metabolism in the Rat"; Biochimica et Biophysica Acta; vol. 544; 1978; pp. 234–244.
Bornstein; "Biological Actions of Synthetic Part Sequences of Human Growth Hormone"; Trends in Biochemical Sciences; vol. 3; 1978; pp. 83–86.
Bornstein; "In Vivo and In Vitro Actions of Synthetic Part Sequences of Human Pituitary Growth Hormone"; Growth Hormone and Related Peptides; Sep. 17–20, 1975; pp. 41–49.
Gertner; "Growth Hormone Actions on Fat Distribution and Metabolism"; Anabolic and Metabolic Effects of Growth Hormone Action; Hormone Research; vol. 38; 1992; pp. 41–43.
Natera et al.; Biochemistry and Molecular Biology International; vol. 33, No. 5; Aug. 1994.
Wijaya et al.; ;Biochemistry and Molecular Biology International; vol. 31, No. 3; Nov. 1993.
Marx; Science; vol. 266; Dec. 2, 1994.
Timthoy; Nature; vol. 372, No. 1; Dec. 1, 1994; pp. 406–407.
Campbell et al.; Proc. Soc. Inper. Biol. Med.; vol. 193; Apr. 1990; pp. 269–273.
Nishikawa et al.; Proc. Engin.; vol. 3, No. 1; 1989; pp. 49–53.
Remingtun's Pharmaceutical Sciences; 18$^{th}$ Edition; 1990; pp. 1633–1636, 1676–1679.

* cited by examiner

Primary Examiner—Christine J. Saoud
(74) Attorney, Agent, or Firm—Foley & Lardner, LLP

(57) ABSTRACT

A method for the treatment of obesity in an animal such as a human, comprises administering to the animal an effective amount of a peptide which comprises an analogue of the carboxyl-terminal sequence of a growth hormone, particularly an analogue of the carboxyl-terminal sequence of human growth hormone containing amino acid residues 177–191. A pharmaceutical composition for use in the treatment of obesity is also disclosed.

8 Claims, 21 Drawing Sheets

SEQUENCE LISTING

```
<160> NUMBER OF SEQ ID NOS: 52

<210> SEQ ID NO 1
<211> LENGTH: 15
<212> TYPE: PRT
<213> ORGANISM: Homo sapiens

<400> SEQUENCE: 1

Leu Arg Ile Val Gln Cys Arg Ser Val Glu Gly Ser Cys Gly Phe
 1               5                  10                  15

<210> SEQ ID NO 2
<211> LENGTH: 21
<212> TYPE: PRT
<213> ORGANISM: Homo sapiens
```

```
<220> FEATURE:
<221> NAME/KEY: MOD_RES
<222> LOCATION: (1)..(3)
<223> OTHER INFORMATION: Arg, His or Lys and may consist of 0-3 residues
<221> NAME/KEY: MOD_RES
<222> LOCATION: (19)..(21)
<223> OTHER INFORMATION: Arg, His or Lys and may consist of 0-3 residues

<400> SEQUENCE: 2

Xaa Xaa Xaa Leu Arg Ile Val Gln Cys Arg Ser Val Glu Gly Ser Cys
 1               5                  10                  15

Gly Phe Xaa Xaa Xaa
            20

<210> SEQ ID NO 3
<211> LENGTH: 15
<212> TYPE: PRT
<213> ORGANISM: Homo sapiens

<400> SEQUENCE: 3

Leu Arg Ile Val Gln Cys Arg Ser Val Glu Gly Ser Cys Gly Phe
 1               5                  10                  15

<210> SEQ ID NO 4
<211> LENGTH: 15
<212> TYPE: PRT
<213> ORGANISM: Homo sapiens

<400> SEQUENCE: 4

Leu Arg Ile Val Gln Cys Arg Ser Val Glu Gly Ser Cys Gly Phe
 1               5                  10                  15

<210> SEQ ID NO 5
<211> LENGTH: 15
<212> TYPE: PRT
<213> ORGANISM: Homo sapiens
<220> FEATURE:
<221> NAME/KEY: MOD_RES
<222> LOCATION: (6)
<223> OTHER INFORMATION: Cys (Acm)
<221> NAME/KEY: MOD_RES
<222> LOCATION: (13)
<223> OTHER INFORMATION: Cys (Acm)

<400> SEQUENCE: 5

Leu Arg Ile Val Gln Cys Arg Ser Val Glu Gly Ser Cys Gly Phe
 1               5                  10                  15

<210> SEQ ID NO 6
<211> LENGTH: 15
<212> TYPE: PRT
<213> ORGANISM: Homo sapiens

<400> SEQUENCE: 6

Leu Arg Lys Val Gln Cys Arg Ser Val Glu Gly Ser Cys Gly Phe
 1               5                  10                  15

<210> SEQ ID NO 7
<211> LENGTH: 15
<212> TYPE: PRT
<213> ORGANISM: Homo sapiens

<400> SEQUENCE: 7

Leu Arg Ile Val Gln Cys Arg Ser Val Glu Gly Ser Cys Gly Phe
 1               5                  10                  15
```

```
<210> SEQ ID NO 8
<211> LENGTH: 15
<212> TYPE: PRT
<213> ORGANISM: Homo sapiens

<400> SEQUENCE: 8

Leu Arg Ile Val Gln Cys Arg Ser Val Glu Gly Ser Cys Gly Phe
 1               5                  10                  15

<210> SEQ ID NO 9
<211> LENGTH: 15
<212> TYPE: PRT
<213> ORGANISM: Homo sapiens

<400> SEQUENCE: 9

Leu Arg Ile Val Gln Cys Ala Ser Val Glu Gly Ser Cys Gly Phe
 1               5                  10                  15

<210> SEQ ID NO 10
<211> LENGTH: 15
<212> TYPE: PRT
<213> ORGANISM: Homo sapiens

<400> SEQUENCE: 10

Leu Arg Ile Val Gln Cys Lys Ser Val Glu Gly Ser Cys Gly Phe
 1               5                  10                  15

<210> SEQ ID NO 11
<211> LENGTH: 15
<212> TYPE: PRT
<213> ORGANISM: Homo sapiens
<220> FEATURE:
<223> OTHER INFORMATION: amide bond between position 7 and 10

<400> SEQUENCE: 11

Leu Arg Ile Val Gln Cys Lys Ser Val Glu Gly Ser Cys Gly Phe
 1               5                  10                  15

<210> SEQ ID NO 12
<211> LENGTH: 15
<212> TYPE: PRT
<213> ORGANISM: Homo sapiens

<400> SEQUENCE: 12

Leu Arg Ile Val Gln Cys Arg Ser Val Glu Gly Ser Cys Gly Phe
 1               5                  10                  15

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (6)
<223> OTHER INFORMATION: Cys (SH)
<221> NAME/KEY: MOD_RES
<222> LOCATION: (13)
<223> OTHER INFORMATION: Cys (SH)

<400> SEQUENCE: 13

Leu Arg Ile Val Gln Cys Arg Ser Val Glu Gly Ser Cys Gly Phe
 1               5                  10                  15

<210> SEQ ID NO 14
<211> LENGTH: 15
<212> TYPE: PRT
<213> ORGANISM: Homo sapiens
```

```
<220> FEATURE:
<221> NAME/KEY: MOD_RES
<222> LOCATION: (11)
<223> OTHER INFORMATION: D-Ala
<221> NAME/KEY: MOD_RES
<222> LOCATION: (14)
<223> OTHER INFORMATION: D-Ala

<400> SEQUENCE: 14

Leu Arg Ile Val Gln Cys Arg Ser Val Glu Ala Ser Cys Ala Phe
 1               5                  10                  15

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (6)
<223> OTHER INFORMATION: Pen (Penicillamine (B,B'-Dimethyl-Cysteine)
<221> NAME/KEY: MOD_RES
<222> LOCATION: (13)
<223> OTHER INFORMATION: Pen (Penicillamine (B,B'-Dimethyl-Cysteine)

<400> SEQUENCE: 15

Leu Arg Ile Val Gln Xaa Arg Ser Val Glu Gly Ser Xaa Gly Phe
 1               5                  10                  15

<210> SEQ ID NO 16
<211> LENGTH: 15
<212> TYPE: PRT
<213> ORGANISM: Homo sapiens

<400> SEQUENCE: 16

Leu Arg Ile Val Gln Cys Arg Ser Val Glu Gly Ser Cys Gly Ala
 1               5                  10                  15

<210> SEQ ID NO 17
<211> LENGTH: 15
<212> TYPE: PRT
<213> ORGANISM: Homo sapiens

<400> SEQUENCE: 17

Leu Arg Ile Val Gln Cys Arg Ser Val Glu Gly Ser Cys Ala Phe
 1               5                  10                  15

<210> SEQ ID NO 18
<211> LENGTH: 15
<212> TYPE: PRT
<213> ORGANISM: Homo sapiens

<400> SEQUENCE: 18

Leu Ala Ile Val Gln Cys Arg Ser Val Glu Gly Ser Cys Gly Phe
 1               5                  10                  15

<210> SEQ ID NO 19
<211> LENGTH: 16
<212> TYPE: PRT
<213> ORGANISM: Homo sapiens

<400> SEQUENCE: 19

Tyr Leu Arg Ile Val Gln Cys Arg Ser Val Glu Gly Ser Cys Gly Phe
 1               5                  10                  15

<210> SEQ ID NO 20
<211> LENGTH: 16
<212> TYPE: PRT
```

<213> ORGANISM: Homo sapiens

<400> SEQUENCE: 20

Lys Leu Arg Ile Val Gln Cys Arg Ser Val Glu Gly Ser Cys Gly Phe
 1               5                  10                  15

<210> SEQ ID NO 21
<211> LENGTH: 15
<212> TYPE: PRT
<213> ORGANISM: Homo sapiens

<400> SEQUENCE: 21

Leu Lys Ile Val Gln Cys Arg Ser Val Glu Gly Ser Cys Gly Phe
 1               5                  10                  15

<210> SEQ ID NO 22
<211> LENGTH: 15
<212> TYPE: PRT
<213> ORGANISM: Homo sapiens

<400> SEQUENCE: 22

Ala Arg Ile Val Gln Cys Arg Ser Val Glu Gly Ser Cys Gly Phe
 1               5                  10                  15

<210> SEQ ID NO 23
<211> LENGTH: 15
<212> TYPE: PRT
<213> ORGANISM: Homo sapiens

<400> SEQUENCE: 23

Leu Arg Ala Val Gln Cys Arg Ser Val Glu Gly Ser Cys Gly Phe
 1               5                  10                  15

<210> SEQ ID NO 24
<211> LENGTH: 15
<212> TYPE: PRT
<213> ORGANISM: Homo sapiens

<400> SEQUENCE: 24

Leu Arg Ile Ala Gln Cys Arg Ser Val Glu Gly Ser Cys Gly Phe
 1               5                  10                  15

<210> SEQ ID NO 25
<211> LENGTH: 15
<212> TYPE: PRT
<213> ORGANISM: Homo sapiens

<400> SEQUENCE: 25

Leu Arg Ile Val Ala Cys Arg Ser Val Glu Gly Ser Cys Gly Phe
 1               5                  10                  15

<210> SEQ ID NO 26
<211> LENGTH: 15
<212> TYPE: PRT
<213> ORGANISM: Homo sapiens

<400> SEQUENCE: 26

Leu Arg Ile Val Gln Ala Arg Ser Val Glu Gly Ser Cys Gly Phe
 1               5                  10                  15

<210> SEQ ID NO 27
<211> LENGTH: 15
<212> TYPE: PRT
<213> ORGANISM: Homo sapiens

<400> SEQUENCE: 27

Leu Arg Ile Val Gln Cys Arg Ala Val Glu Gly Ser Cys Gly Phe
1               5                   10                  15

<210> SEQ ID NO 28
<211> LENGTH: 15
<212> TYPE: PRT
<213> ORGANISM: Homo sapiens

<400> SEQUENCE: 28

Leu Arg Ile Val Gln Cys Arg Ser Ala Glu Gly Ser Cys Gly Phe
1               5                   10                  15

<210> SEQ ID NO 29
<211> LENGTH: 15
<212> TYPE: PRT
<213> ORGANISM: Homo sapiens

<400> SEQUENCE: 29

Leu Arg Ile Val Gln Cys Arg Ser Val Ala Gly Ser Cys Gly Phe
1               5                   10                  15

<210> SEQ ID NO 30
<211> LENGTH: 15
<212> TYPE: PRT
<213> ORGANISM: Homo sapiens

<400> SEQUENCE: 30

Leu Arg Ile Val Gln Cys Arg Ser Val Glu Ala Ser Cys Gly Phe
1               5                   10                  15

<210> SEQ ID NO 31
<211> LENGTH: 15
<212> TYPE: PRT
<213> ORGANISM: Homo sapiens

<400> SEQUENCE: 31

Leu Arg Ile Val Gln Cys Arg Ser Val Glu Gly Ala Cys Gly Phe
1               5                   10                  15

<210> SEQ ID NO 32
<211> LENGTH: 15
<212> TYPE: PRT
<213> ORGANISM: Homo sapiens

<400> SEQUENCE: 32

Leu Arg Ile Val Gln Cys Arg Ser Val Glu Gly Ser Ala Gly Phe
1               5                   10                  15

<210> SEQ ID NO 33
<211> LENGTH: 17
<212> TYPE: PRT
<213> ORGANISM: Homo sapiens

<400> SEQUENCE: 33

Lys Lys Leu Arg Ile Val Gln Cys Arg Ser Val Glu Gly Ser Cys Gly
1               5                   10                  15

Phe

<210> SEQ ID NO 34
<211> LENGTH: 26
<212> TYPE: PRT
<213> ORGANISM: Homo sapiens

```
<400> SEQUENCE: 34

Phe Arg Lys Asp Met Asp Lys Val Glu Thr Phe Leu Arg Ile Val Gln
 1               5                  10                  15
Cys Arg Ser Val Glu Gly Ser Cys Gly Phe
            20                  25

<210> SEQ ID NO 35
<211> LENGTH: 26
<212> TYPE: PRT
<213> ORGANISM: Homo sapiens

<400> SEQUENCE: 35

Phe Arg Lys Asp Met Asp Lys Val Glu Thr Phe Leu Arg Ile Val Gln
 1               5                  10                  15
Cys Arg Ser Val Glu Gly Ser Cys Gly Phe
            20                  25

<210> SEQ ID NO 36
<211> LENGTH: 26
<212> TYPE: PRT
<213> ORGANISM: Homo sapiens

<400> SEQUENCE: 36

Phe Arg Lys Asp Met Asp Lys Val Glu Thr Phe Leu Arg Met Val Gln
 1               5                  10                  15
Cys Arg Ser Val Glu Gly Ser Cys Gly Phe
            20                  25

<210> SEQ ID NO 37
<211> LENGTH: 26
<212> TYPE: PRT
<213> ORGANISM: Rhesus sp.

<400> SEQUENCE: 37

Phe Arg Lys Asp Met Asp Lys Ile Glu Thr Phe Leu Arg Ile Val Gln
 1               5                  10                  15
Cys Arg Ser Val Glu Gly Ser Cys Gly Phe
            20                  25

<210> SEQ ID NO 38
<211> LENGTH: 27
<212> TYPE: PRT
<213> ORGANISM: Rattus sp.

<400> SEQUENCE: 38

Phe Lys Lys Asp Leu His Lys Ala Glu Thr Tyr Leu Arg Val Met Lys
 1               5                  10                  15
Cys Arg Arg Phe Ala Glu Ser Ser Cys Ala Phe
            20                  25

<210> SEQ ID NO 39
<211> LENGTH: 27
<212> TYPE: PRT
<213> ORGANISM: Mus sp.

<400> SEQUENCE: 39

Phe Lys Lys Asp Leu His Lys Ala Glu Thr Tyr Leu Arg Val Met Lys
 1               5                  10                  15
Cys Arg Arg Phe Val Glu Ser Ser Cys Ala Phe
            20                  25
```

<210> SEQ ID NO 40
<211> LENGTH: 27
<212> TYPE: PRT
<213> ORGANISM: Cricetidae sp.

<400> SEQUENCE: 40

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 41
<211> LENGTH: 27
<212> TYPE: PRT
<213> ORGANISM: Squalus sp.

<400> SEQUENCE: 41

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 42
<211> LENGTH: 27
<212> TYPE: PRT
<213> ORGANISM: Squalus sp.

<400> SEQUENCE: 42

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 43
<211> LENGTH: 27
<212> TYPE: PRT
<213> ORGANISM: Unknown Organism
<220> FEATURE:
<223> OTHER INFORMATION: Description of Unknown Organism: Fox, dog, cat

<400> SEQUENCE: 43

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 44
<211> LENGTH: 27
<212> TYPE: PRT
<213> ORGANISM: Mustela sp.

<400> SEQUENCE: 44

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 45
<211> LENGTH: 27
<212> TYPE: PRT
<213> ORGANISM: Capitalis sp.

<400> SEQUENCE: 45

```
Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25
```

<210> SEQ ID NO 46
<211> LENGTH: 27
<212> TYPE: PRT
<213> ORGANISM: Ovis sp.

<400> SEQUENCE: 46

```
Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25
```

<210> SEQ ID NO 47
<211> LENGTH: 27
<212> TYPE: PRT
<213> ORGANISM: Haedus sp.

<400> SEQUENCE: 47

```
Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25
```

<210> SEQ ID NO 48
<211> LENGTH: 27
<212> TYPE: PRT
<213> ORGANISM: Sus scrofa

<400> SEQUENCE: 48

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25
```

<210> SEQ ID NO 49
<211> LENGTH: 27
<212> TYPE: PRT
<213> ORGANISM: Lama pacos

<400> SEQUENCE: 49

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25
```

<210> SEQ ID NO 50
<211> LENGTH: 27
<212> TYPE: PRT
<213> ORGANISM: Equus caballus

<400> SEQUENCE: 50

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25
```

<210> SEQ ID NO 51
<211> LENGTH: 27

```
<212> TYPE: PRT
<213> ORGANISM: Elephantus sp.

<400> SEQUENCE: 51

Phe Lys Lys Asp Leu His Lys Ala Glu Thr Tyr Leu Arg Val Met Lys
  1               5                  10                  15

Cys Arg Arg Phe Val Glu Ser Ser Cys Ala Phe
             20                  25

<210> SEQ ID NO 52
<211> LENGTH: 27
<212> TYPE: PRT
<213> ORGANISM: Unknown Organism
<220> FEATURE:
<223> OTHER INFORMATION: Description of Unknown Organism: Ancestral
      mammal

<400> SEQUENCE: 52

Phe Lys Lys Asp Leu His Lys Ala Glu Thr Tyr Leu Arg Val Met Lys
  1               5                  10                  15

Cys Arg Arg Phe Val Glu Ser Ser Cys Ala Phe
             20                  25
```

TREATMENT OF OBESITY

This application claims priority to international application PCT/AU98/00724, filed on Sep. 4, 1998, designating the United States of America, and published on Mar. 18, 1999, in the English language in accordance with PCT Article 21(2) as WO 099/12969, and Australian Provisional Patent Application Nos. PO 9001 filed Sep. 8, 1997 and PP 0398 filed Nov. 13, 1997.

FIELD OF THE INVENTION

This invention relates to the treatment of obesity in animals. In particular, the invention relates to the treatment of obesity in humans, although it is to be understood that the present invention also extends to the treatment of obesity in non-human mammals, for example, for the improvement of meat qualities in farm animals used in food production.

BACKGROUND OF THE INVENTION.

The critical role of human growth hormone (hGH) in postnatal growth in humans is well recognised. Less obvious is the impact of this hormone on the regulation of lipid and carbohydrate metabolism, due to lack of detailed molecular studies.

It is well documented that the predominant form of hGH is a globular protein with a molecular weight of 22,000 daltons (22-KD) and consists of 191 amino acid residues in a single-chain, folded by 2 disulphide bonds with a small loop at the carboxyl terminus between residues 182 and 189. Recent crystallographic studies also show that the hGH molecule contains four anti-parallel α-helices which are arranged in a left-twisted, tightly-packed helical bundle[1]. The concept that there are discrete functional domains within the hGH molecule responsible for specific metabolic actions of the hormone is generally accepted. The amino-terminus has been identified as the functional domain responsible for the insulin-like actions of the hGH molecule[2,3].

Recombinant DNA technology opens the way to the large-scale commercial production of human growth hormone, and the recombinant hGH appears to have equivalent biological efficacies and pharmacokinetic properties[4,5]. Current supply of this multiple-functional hormone no longer restricts the types and numbers of experimental therapies in humans and animals. The use of hGH for treatment of short stature in children and adults is well-established[6]. Therapeutic effects of hGH in female infertility have also been reported[7,8]. Treatment of human obesity with hGH encounters a variety of problems. Evidence suggests that this multiple-functional hormone often simultaneously exerts in vivo, by various bioactive domains within the molecules, some adverse effects[9,10].

Regulation of lipid metabolism by GH was first described in 1959 by Raben & Holienberg[11]. The regulatory role of the hormone in lipid metabolism was subsequently supported by the body composition studies of GH-deficient and GH-treated humans[12,13] and pigs[14,15]. The findings of Gertner suggest that hGH is linked to adipose tissue distribution through a series of interactions known as the "GH-fat cycle"[16]. However, the molecular events transpiring to these biochemical and physiological changes remained largely unknown. The metabolic effects of GH on adipose and other tissues in vivo are variable and complex, apparently consisting of at least two components, an early insulin-like effect followed by a later more profound anti-insulin effect[17]. The results of the latter effect may include both a stimulation of lipolysis and an inhibition of lipogenesis. The anti-lipogenic effect of hGH has been substantiated with the demonstrations of the decrease of the expression of glucose transporter GLUT 4 in adipocytes[18], the inhibition of the activity of acetyl-CoA carboxylase in adipose tissues[19,20] and the reduction of glucose incorporation into lipid in both isolated cells and tissues[21,22].

In view of the multiple-functional effects of intact hGH and the problems encountered in clinical applications of the intact hormone, work leading to the present invention has been directed to investigating whether hGH derivatives could be synthesised that retain the desired bioactivities and lack the unwanted side effects.

The structure-function studies of hGH with synthetic hormonal fragments have revealed that the carboxyl terminus of the hGH molecule appears to be the functional domain of the hormone for the regulation of lipid metabolism[20,23] and it has been shown that a synthetic peptide having a sequence based in the carboxyl terminal region reduces body weight gain and adipose tissue mass in a laboratory obese animal model.

The entire contents of U.S. Pat. No. 5,869,452, issued on application Ser. No. 08/340389, dated Nov. 15, 1994, including the specification, claims and figures, are incorporated herein by reference in their entirety.

SUMMARY OF THE INVENTION

The present invention provides a peptide which comprises an analogue of the carboxyl-terminal sequence of a growth hormone. The peptide may comprise an analogue of the carboxyl-terminal sequence of human growth hormone or the growth hormone of a non-human mammalian species. As described above, the carboxyl-terminal sequence of growth hormone includes a bioactive lipid metabolic domain. In one embodiment of the invention, the peptide comprises an analogue of the carboxyl-terminal sequence of human growth hormone containing amino acid residues 177–191 or a corresponding sequence of a non-human mammalian growth hormone. The analogue may be obtained by insertion, deletion or substitution of amino acids in, or chemical modification of, the native carboxyl-terminal sequence of human growth hormone or the growth hormone of a non-human mammalian species.

In another aspect, the present invention provides a method for treating obesity comprising administering an effective amount of a peptide which comprises an analogue of the carboxyl-terminal sequence of a growth hormone, as described above. The treatment may be administered to any animal, including humans.

The present invention also provides a pharmaceutical composition for use in the treatment of obesity comprising an effective amount of a peptide which comprises an analogue of the carboxyl-terminal sequence of a growth hormone as described above, together with one or more pharmaceutically acceptable carriers and/or diluents.

In yet another aspect, the present invention provides use of a peptide which comprises an analogue of the carboxyl-terminal sequence of a growth hormone as described above, in the manufacture of a pharmaceutical composition for the treatment of obesity in an animal.

DESCRIPTION OF THE PREFERRED EMBODIMENTS

According to one aspect of the present invention, there is provided a method for the treatment of obesity in an animal, which comprises administering to the animal an effective amount of a peptide which comprises an analogue of the carboxyl-terminal sequence of a growth hormone.

Preferably, the animal is a human although the invention also extends to the treatment of non-human mammals Preferably also, the peptide comprises an analogue of the carboxyl-terminal sequence of human growth hormone containing amino acid residues 177–191 (hereinafter referred to as hGH 177–191). Alternatively, the peptide may comprise an analogue of the carboxyl-terminal sequence of the growth hormone of other non-human mammalian species, such as bovine, porcine, ovine, equine, feline or canine growth hormone, corresponding to the hGH 177–191 peptide.

As used throughout this specification, the term "obesity" is used to include both excess body weight and excess adipose tissue mass in the animal, and correspondingly the references to treatment of obesity include both reduction of body weight gain and reduction of adipose tissue mass of the obese animal.

The expected outcome of any treatment of obesity is the reduction of body weight, body adipose tissue mass in particular. The reduction of body adipose tissue mass is directly regulated by two biochemical processes—lipogenesis (fat-production) and lipolysis (fat-reduction)—and it is generally understood that these biochemical processes are controlled by key metabolic enzymes, specifically the fat-reducing key enzyme (hormone-sensitive lipase) and the fat-producing key enzyme (acetyl CoA carboxylase).

It has been shown by the present inventors that hGH 177–191 is effective in stimulating the fat-reducing key enzyme, hormone-sensitive lipase, and in inhibiting the fat-producing key enzyme, acetyl CoA carboxylase. This is further supported by data showing that in the presence of hGH 177–191, fat utilization is accelerated while fat production is reduced, as measured by metabolic end-products in vitro as well as in vivo. In addition, the mechanism of these molecular actions has been established as resulting from the activation of the production of the cellular second-messenger, diacylglycerol.

It will, of course, be appreciated that the present invention extends to the use of peptides which are analogues of longer amino acid sequences than the particular sequence 177–191 of growth hormone, for example analogues of the sequence 172–191 of human growth hormone or the corresponding sequence of growth hormone of other non-human mammalian species.

The concept of correspondence in amino acid sequences between species is well known in the biological sciences and is determined by aligning comparable sequences (including if necessary theoretical deletions) to match isofunctional or isostereo amino acids thereby maximizing homology. The published corresponding sequences of the C-terminus region of the growth hormone of selected mammals are tabulated below[26], using standard single letter notation: (SEQ ID NOS 34–52, respectively in order of appearance).

| GH Species | Sequence Position 170 | 180 | 190 | Sequence Identifier |
|---|---|---|---|---|
| human | FRKDMDKVETFLRIYQCR.SVEGSCGF | | | Sequence ID No. 34 |
| human variant | FRKDMDKVETFLRWQCR.SVEGSCGF | | | Sequence ID No. 35 |
| human CS | FRKDMDKVETFLRMVQCR.SVEGSCGF | | | Sequence ID No. 36 |
| monkey, rhesus | FRKDMDKIETFLRIVQCR.SVEGSCGF | | | Sequence ID No. 37 |
| rat | FKKDLHKAETYLRVMKCRRFAESSCAF | | | Sequence ID No. 38 |
| mouse | FKKDLHKAETYLRVMKCRRFVESSCAF | | | Sequence ID No. 39 |
| hamster | FKKDLHKAETYLRVMKCRRFVESSCAF | | | Sequence ID No. 40 |
| whale, fin | FKKDLHKAETYLRVMKCRRFVESSCAF | | | Sequence ID No. 41 |
| whale, sei | FKKDLHKAETYLRVMKCRRFVESSCAF | | | Sequence ID No. 42 |
| fox, dog, cat | FKKDLHKAETYLRVMKCRRFVESSCAF | | | Sequence ID No. 43 |
| mink | FKKDLHKAETYLRVMKCRRFVESSCAF | | | Sequence ID No. 44 |
| cattle | FRKDLHKTETYLRVMKCRRFGEASCAF | | | Sequence ID No. 45 |
| sheep | FRKDLHKTETYLRVMKCRRFGEASCAF | | | Sequence ID No. 46 |
| goat | FRKDLHKTETYLRVMKCRRFGEASCAF | | | Sequence ID No. 47 |
| pig | FKKDLHKAETYLRVMKCRRFVESSCAF | | | Sequence ID No. 48 |
| alpaca | FKKDLHKAETYLRVMKCRRFVESSCAF | | | Sequence ID No. 49 |
| horse | FKKDLHKAETYLRVMKCRRFVESSCAF | | | Sequence ID No. 50 |
| elephant | FKKDLHKAETYLRVMKCRRFVESSCAF | | | Sequence ID No. 51 |
| ancestral mammal | FKKDLHKAETYLRVMKCRRFVESSCAF | | | Sequence ID No. 52 |

The present invention extends to the use of peptides which are analogues of the native carboxyl-terminal sequences of human growth hormone or growth hormone of other animal species, and which are derived from natural or synthetic (including recombinant) sources, provided always that the resulting peptide retains the biological activity of the native carboxyl-terminal sequence described herein, namely the ability to reduce body weight gain and adipose tissue mass in an obese animal. In particular, these analogues may exhibit a cyclic configuration, which may be induced by a disulfide bond.

The analogues of the present invention may be derived by elongation, insertion, deletion or substitution of amino acids in, or chemical modification of, or introduction of a cyclic amide bond between the side chains of amino acids of, the native carboxyl-terminal sequence. Amino acid insertional analogues include amino and/or carboxylic terminal fusions as well as intra-sequence insertions of single or multiple (for example, up to 10, preferably up to 5) amino acids. Insertional amino acid sequence analogues are those in which one or more amino acid residues are introduced into a predetermined site in the protein although random insertion is also possible with suitable screening of the resulting product. Deletional analogues are characterised by the removal of one or more (for example, up to 5, preferably up to 3) amino acids from the sequence. Substitutional amino acid analogues are those in which at least one amino acid residue in the sequence, preferably one or two, has been replaced by another of the twenty primary protein amino acids, or by a non-protein amino acid. Chemical modifications of the native carboxyl-terminal sequence include the acetylation of the amino-terminus and/or amidation of the carboxyl-terminus and/or side chain cyclisation of the native carboxyl-terminal sequence.

Analogues of the native carboxyl-terminal sequences of human growth hormone or growth hormone of other animal species which in particular retain the same conformation, structure and charge characteristics as the native carboxyl-terminal sequences can be expected to exhibit the same or similar biological activity as the native sequences, in particular in the ability to reduce body weight gain and adipose tissue mass in an obese animal.

Whilst the following detailed description refers specifically to analogues of hGH 177–191, it is to be understood that this invention extends to similar analogues of corresponding peptides of non-human mammalian growth hormone as described above.

Peptides comprising amino acid residues 177–191 of native human growth hormone (hGH 177–191) include the following sequence (Ref No. 9401):

Leu-Arg-Ile-Val-Gln-Cys-Arg-Ser-Val-Glu-Gly-Ser-Cys-Gly-Phe (SEQ ID NO: 1)

Such a native peptide may be in cyclic disulfide form, and may comprise an organic or inorganic acid addition salt.

Analogues of the hGH 177–191 peptide may be obtained by deletion or insertion of one or more amino acid residues at any position along the native sequence, with the retention of anti-obesity properties as described above. Preferably, the analogue is in a cyclic configuration.

Alternatively, analogues of the hGH 177–191 peptide may be obtained by substitution of one or more amino acid residues at any position along the native sequence.

Screening for in vitro and in vivo activity using alanine substitution scanning and other methods reported herein has revealed positions and relationships between amino acids in hGH 177–191 which are important in the bioactivity as described above. Preferred analogues of the current invention include peptide analogues of hGH 177–191 wherein (i) amino acids at positions 182 and 189 of hGH are joined by a bond to promote a cyclic conformation; and/or (ii) amino acids at positions 183 and 186 of hGH are joined by a salt bridge or a covalent bond.

The bond between amino acids at 182 and 189 of hGH may be a disulfide bond, in which case the amino acids at positions 182 and 189 of hGH may preferably be L- or D-Cys or Pen.

When the amino acids at positions 183 and 186 of hGH are joined by a salt bridge, these amino acids may preferably be (X and Y) or (Y and X), respectively, where:

X is a positively charged amino acid such as L- or D-Arg, Lys or Orn and

Y is a negatively charged amino acid such as L- or D-Asp or Glu.

When the amino acids at positions 183 and 186 of hGH are joined by a covalent bond, that bond may be an amide bond in which case these amino acids may preferably be (X and Y) or (Y and X), respectively, where:

X is selected from the group consisting of L- or D-Lys and Orn and

Y is selected from the group consisting of L- or D-Asp and Glu.

The amino acid at position 178 of hGH is preferably a positively charged amino acid such as L- or D-Arg, Lys or Orn.

Analogues may also be obtained by elongation of the native hGH 177–191 peptide sequence at one or both ends of the amino acid residues, for example with one or more hydrophilic amino acids to increase solubility in aqueous solution. Such analogues include the following sequence, preferably in cyclic disulphide form:

$X^1$m-Leu-Arg-Ile-Val-Gln-Cys-Arg-Ser-Val-Glu-Gly-Ser-Cys-Gly-Phe-$X^2$n (SEQ ID NO: 2)

wherein $X^1$ and $X^2$ are each is selected from the group consisting of L- or D-Arg, His and Lys, and m and n are each 0, 1, 2 or 3 with the provision that at least m or n is 1.

Throughout this specification, elements which are underlined denote differences from the native hGH 177–191 sequence, and unless otherwise stated, amino acids at positions corresponding to 182 and 189 are joined by a disulfide bond.

One elongation analogue not elongated with a hydrophilic amino acid but nonetheless exhibiting especially enhanced anti-obesity properties is the following (Ref No. 9604):

Tyr-Leu-Arg-Ile-Val-Gln-Cys-Arg-Ser-Val-Glu-Gly-Ser-Cys-Gly-Phe. (SEQ ID NO: 19)

Analogues may also be obtained by chemical modification of the native hGH 177–191 peptide sequence. Such analogues include the sequence:

$Y^1$-Leu-Arg-Ile-Val-Gln-Cys-Arg-Ser-Val-Glu-Gly-Ser-Cys-Gly-Phe (SEQ ID NO: 3)

wherein $Y^1$ is selected from the group consisting of the desamino form (H), acetyl ($CH_3CO$—) and other acyl groups; or the sequence:

Leu-Arg-Ile-Val-Gln-Cys-Arg-Ser-Val-Glu-Gly-Ser-Cys-Gly-Phe-$Y^2$ (SEQ ID NO: 4)

where $Y^2$ is selected from the group consisting of —$CONH_2$ and alkyl amide groups.

Specific hGH 177–191 analogues obtained by substitution of amino acids, by elongation, by chemical modification, or by introduction of a cyclic amide bond between side chains of amino acids, of the native hGH 177–191 peptide sequence, and which exhibit anti-obesity properties, include the following:

| Ref No. | STRUCTURE | SEQ ID NO: |
|---|---|---|
| 9502 | Leu Arg Ile Val Gln Pen Arg Ser Val Glu Gly Ser Pen Gly Phe | 15 |
| 9405 | CH₃CO— Leu Arg Ile Val Gln Cys Arg Ser Val Glu Gly Ser Cys Gly Phe | 8 |
| 9410 | H — Leu Arg Ile Val Gln Cys Arg Ser Val Glu Gly Ser Cys Gly Phe | 12 |
| 9404 | Leu Arg Ile Val Gln Cys Arg Ser Val Glu Gly Ser Cys Gly Phe — CONH₂ | 7 |

-continued

| Ref No. | STRUCTURE | SEQ ID NO: |
|---|---|---|
| 9407 | Leu Arg Ile Val Gln Cys <u>Lys</u> Ser Val Glu Gly Ser Cys Gly Phe | 10 |
| 9408 | Leu Arg Ile Val Gln Cys <u>Lys</u> Ser Val Glu Gly Ser Cys Gly Phe (amide bond) | 11 |
| 9604 | <u>Tyr</u> Leu Arg Ile Val Gln Cys Arg Ser Val Glu Gly Ser Cys Gly Phe | 19 |
| 9605 | <u>Lys</u> Leu Arg Ile Val Gln Cys Arg Ser Val Glu Gly Ser Cys Gly Phe | 20 |
| 9618 | <u>Lys Lys</u> Leu Arg Ile Val Gln Cys Arg Ser Val Glu Gly Ser Cys Gly Phe | 33 |
| 9607 | <u>Ala</u> Arg Ile Val Gln Cys Arg Ser Val Glu Gly Ser Cys Gly Phe | 22 |
| 9606 | Leu <u>Lys</u> Ile Val Gln Cys Arg Ser Val Glu Gly Ser Cys Gly Phe | 21 |
| 9608 | Leu Arg <u>Ala</u> Val Gln Cys Arg Ser Val Glu Gly Ser Cys Gly Phe | 23 |
| 9403 | Leu Arg <u>Lys</u> Val Gln Cys Arg Ser Val Glu Gly Ser Cys Gly Phe | 6 |
| 9609 | Leu Arg Ile <u>Ala</u> Gln Cys Arg Ser Val Glu Gly Ser Cys Gly Phe | 24 |
| 9610 | Leu Arg Ile Val <u>Ala</u> Cys Arg Ser Val Glu Gly Ser Cys Gly Phe | 25 |
| 9612 | Leu Arg Ile Val Gln Cys Arg <u>Ala</u> Val Glu Gly Ser Cys Gly Phe | 27 |
| 9613 | Leu Arg Ile Val Gln Cys Arg Ser <u>Ala</u> Glu Gly Ser Cys Gly Phe | 28 |
| 9615 | Leu Arg Ile Val Gln Cys Arg Ser Val Glu <u>Ala</u> Ser Cys Gly Phe | 30 |
| 9616 | Leu Arg Ile Val Gln Cys Arg Ser Val Glu Gly <u>Ala</u> Cys Gly Phe | 31 |
| 9602 | Leu Arg Ile Val Gln Cys Arg Ser Val Glu Gly Ser Cys <u>Ala</u> Phe | 17 |
| 9501 | Leu Arg Ile Val Gln Cys Arg Ser Val Glu <u>D-Ala</u> Ser Cys <u>D-Ala</u> Phe | 14 |
| 9601 | Leu Arg Ile Val Gln Cys Arg Ser Val Glu Gly Ser Cys Gly <u>Ala</u> | 16 | wherein the amino acid residue abbreviations used are in accordance with the standard peptide nomenclature:

| | | | |
|---|---|---|---|
| Gly = | Glycine; | Ile = | Isoleucine; |
| Glu = | Glutamic Acid; | Phe = | Phenylalanine; |
| Cys = | Cysteine; | Arg = | Arginine; |
| Gln = | Glutamine; | Leu = | Leucine; |
| Ser = | Serine; | Val = | Valine; |
| Lys = | Lysine; | Ala = | Alanine; |
| Asp = | Aspartic acid; | His = | Histidine; |
| Orn = | Ornithine; | Tyr = | Tyrosine; |
| Pen = | Penicillamine (β,β'-Dimethyl-Cysteine) | | |

All amino acids, except for glycine, are of the L-absolute configuration, unless indicated as D-absolute configuration. All the above peptides above have a cyclic disulfide bond between Cys(182) and Cys(189) or Pen(182) and Pen(189) as a appropriate.

Where appropriate, the analogues described above may comprise an organic or inorganic acid addition salt.

The term "effective amount" as used herein means an amount of the peptide sufficient to attain the desired effect in the treatment of obesity in the animal, but not so large an amount as to cause serious side effects or adverse reactions.

In another aspect, the present invention provides the use of a peptide which comprises an analogue of the carboxyl-terminal sequence of a growth hormone as described above, in the treatment of obesity in an animal or in the manufacture of a pharmaceutical composition for the treatment of obesity in an animal.

In yet another aspect, the present invention provides a pharmaceutical composition for use in the treatment of obesity in an animal, comprising an effective amount of a peptide which comprises an analogue of the carboxyl-terminal sequence of a growth hormone as described above, together with one or more pharmaceutically acceptable carriers and/or diluents.

The peptide which is the active ingredient of the pharmaceutical composition of this aspect of the invention exhibits advantageous therapeutic activity in the treatment of obesity in an animal when administered in an amount appropriate to the particular case. For example, from about 0.5 μg to about 20 mg per kilogram of body weight per day may be administered. Dosage regimens may be adjusted to provide the optimum prophylactic or therapeutic response. For example, one or more divided doses may be administered daily, weekly, monthly or in other suitable time intervals or the dose may be proportionally reduced as indicated by the exigencies of the clinical situation.

The active ingredient may be administered in any convenient manner such as by the oral, parenteral (including intraperitoneal, intravenous, subcutaneous, intramuscular and intramedullary injection), intranasal, intradermal or suppository routes or by implanting (eg using slow release devices). For ease of administration, oral administration is preferred, however parenteral administration is also quite convenient Depending on the route of administration, the active ingredient may be required to be coated in a material that protects said ingredient from the action of enzymes, acids and other natural conditions which may inactivate the said ingredient. For example, low lipophilicity of the ingredient may allow it to be destroyed in the gastrointestinal tract by enzymes capable of cleaving peptide bonds and in the stomach by acid hydrolysis. In order to administer the composition by other than parenteral administration, the active ingredient may be coated by, or administered with, a material to prevent its inactivation.

The active ingredient may also be administered in dispersions prepared in glycerol, liquid polyethylene glycols, and/or mixtures thereof and in oils. Under ordinary conditions of storage and use, these preparations will usually contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thiomorosal, and the like. In many cases, it will be preferable to include isotonic agents, for example, sugars or sodium chloride. Prolonged absorption of the injectable compositions can be brought about by, for example, the use in the compositions of agents delaying absorption.

Sterile injectable solutions are prepared by incorporating the active ingredient in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral administration, the active ingredient may be incorporated with excipients and used in the form of ingestible tablets, buccal tablets, troches, capsules, elixirs, suspensions, syrups, wafers, and the like. Such compositions and preparations should contain at least 0.01% by weight and more preferably at least 0.1–1% by weight of active ingredient. The percentage of the compositions and preparations may, of course, be varied and may conveniently be between about 5 to about 80% of the weight of the unit. The amount of active ingredient in the pharmaceutical compositions is such that a suitable dosage will be obtained. Preferred compositions or preparations according to the present invention may, for example, be prepared so that an oral dosage unit form contains between about 0.5 $\mu$g and 200 mg and more preferably 10 $\mu$g and 20 mg of active ingredient.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient may be incorporated into sustained-release preparations and formulations.

As used herein, pharmaceutically acceptable carriers and diluents include any and all solvents, dispersion media, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmnaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the treatment of obesity.

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

Further details of the present invention will be apparent from the following Example and the accompanying drawings which are included by way of illustration, not by way of limitation, of this invention.

EXAMPLE

Materials and Methods

Figure 1A:
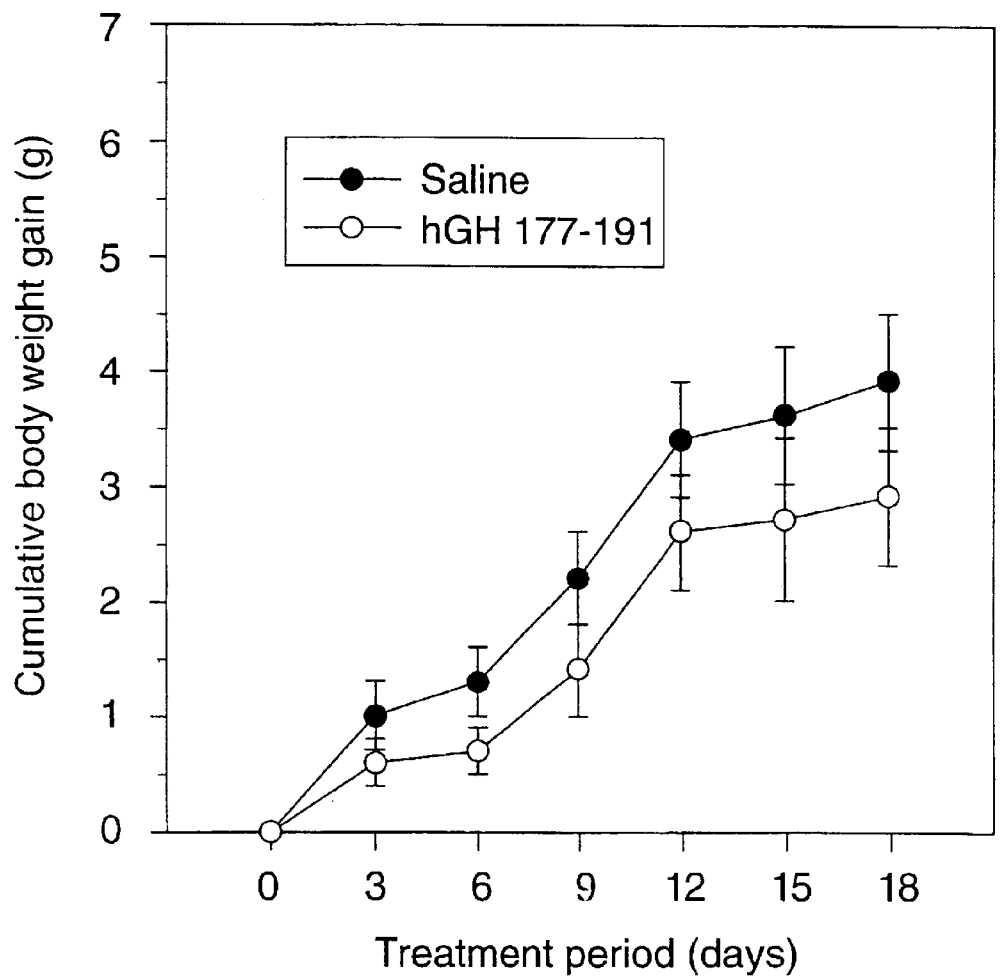
FIGS. 1A & 1B show the effect of hGH 177–191 peptide on cumulative body weight gains in male (1A) and female (1B) C57BL/6J (ob/ob) mice during the 18-day treatment period. Animals were given a daily intraperitoneal injection of 0.1 ml of either saline or hGH 177–191 (200 $\mu$g/kg body weight). Each points represents the mean±SEM of 6 animals.

Animals and Treatments.

Obese C57BL/6J (ob/ob) mice and fatty Zucker (fa/fa) rats were used to demonstrate the biological effects of the synthetic hGH 177–191 and analogues. The animals of the same age and same sex were randomly divided into two groups, housed 6 per cage and maintained on a normal 12-hr light/dark cycle at a constant room temperature of 25° C. in the animal house of the Department of Biochemistry and—Molecular Biology, Monash University, Clayton, Australia. Animals were fed ad libitum on pre-determined quantity of animal pellets (Clark King, Melboume, Australia) and allowed free access to water at all times. The animals were given a daily intraperitoneal (i.p) injection of 0.1 ml of either the synthetic peptide (200–500 µg/kg body weight) or equivalent volume of physiological saline (0.9% sodium chloride) for appropriate number of days. The i.p. injection was administered with a 30G×½" (0.31×13 mm) needle on a 1-ml disposable tuberculin syringes, and the site of injection was the lower left quadrant of the abdomen of the animals. To study the effects of controlled-delivery of hGH 177–191 and analogues, slow-release peptide-pellets in a diameter of 3 mm were implanted intradermally in the abdominal region of Zucker rats under anaesthesia. The body weight and food intake were monitored for the periods of time as indicated.

Peptide Synthesis

The peptides of the present invention were prepared by using standard 9-fluorenylmethyloxycarbonyl(Fmoc) solid-phase techniques. The solid-phase synthesis, for example, could be commenced from the C-terminal end of the peptide using an a-amino protected amino acid. A suitable starting materials could be prepared, for instance, by attaching the required α-amino acid to a Wang resin (4-alkoxybenzyl alcohol resin), or Rink amide resin (2,4-dimethoxy4'-[carboxymethyoxy]-benzhydrylamine linked to amino methyl resin) or PAM resin (4-hydroxymethylphenyl-acetic acid resin). Resins were commercially available from Auspep Pty. Ltd., Parkville, Victoria, Australia.

In the solid-phase preparation of the compounds of this invention, a protected amino acid was coupled to a resin with the aid of a coupling agent After the initial coupling, the α-amino protecting group was removed by piperidine in organic solvents at room temperature. Following the removal of the α-amino protecting group, the remaining protected amino acids were coupled stepwise in the desired order. A 4-fold excess of each protected amino acid was generally used in the reaction with an appropriate carboxyl group activator such as diisopropylcarbodiimide (DIC) and 1-hydroxybenzotriazole (HOBt), in methylene chloride (DCM)-N,N-dimethylformamide (DMF) mixtures.

After the desired amino acid sequence was completed, the peptide was then cleaved from the resin support by treatment with a reagent such as trifluoroacetic acid (TFA) or trifluormethanesulfonic acid (TFMSA) which cleaved the peptide from the resin, as well as all side-chain protecting groups, except for Cys(Acm). When a Wang resin was used, TFA treatment resulted in the formation of the free peptide acids. When the Rink amide resin was used, TFA treatment resulted in the formation of the free peptide amides. When a PAM resin was used, TFMSA treatment resulted in the formation of the free peptide acids. The target peptides might exist in cyclic disulfide form which requires post-synthesis modification.

The following examples are provided for the purpose of further illustration only and not intended to be limitations on the disclosed invention.

A. Synthesis of pentadecapeptide comprising amino acid residues 177–191 of native human growth hormone, designated as hGH (177–191) (Ref No. 9401): (SEQ ID NO: 1).

$Leu^1$-Arg-Ile-Val-Gln-Cys-Arg-Ser-Val-Glu-Gly-Ser-Cys-Gly-$Phe^{15}$ (cyclic disulfide)

The following procedure was employed in preparing the pentadecapeptide:

Step 1. Wang resin (0.625 g, 0.5 mmol) was placed in a 10 ml-reaction vessel. DCM (4 ml) was added to the reaction vessel. The Wang resin was washed with vigorous stirring for 2 minutes. The DCM solution was then drained from the reaction vessel. This washing was repeated twice.

Step 2. Fmoc-L-phenylalanine (Fmoc-Phe, 0.388 g, 1.0 mmol) in 2.4 ml NMP-DCM (1:5, v/v) and DIC (0.135 g, 1.0 mmol) in 1.0 ml NMP were mixed in a reaction vessel for 10 minutes. To the mixture, 4-dimethylaminopyridine (DMAP, 0.074g, 0.06 mmol) in 0.6 ml DMF was added. The reaction in the solution was allowed to continue for 68 minutes at room temperature. The solution was then drained, the resin was washed thoroughly with NMP (4 ml×3) and DCM (4 ml×3). The Fmoc-Phe-Wang Resin complex was dried in vacuo overnight to yield 0.781 g of material. The coupling level of amino acid to resin was determined to be 0.80 mmol/g resin by using spectrophotometric measurement of the Fmoc-piperidine adduct.

Step 3. Fmoc-Phe-Wang Resin (0.263 g, 0.20 mmol) was placed in the 10 ml-reaction vessel. DMF (8 ml) was added to wash and swell the resin by stirring for 2 minutes. The solution was then drained from the reaction vessel.

Step 4. A 25% piperidine/DMF solution (4 ml) was added to the reaction vessel. The resulting mixture was stirred for 2 minutes. The solution was drained from the reaction vessel. This deprotection procedure was repeated once but with prolonged stirring time (18 min). The solution was drained from the reaction vessel.

Step 5. DMF (8 ml) was added to the reaction vessel. The resulting solution was stirred for 2 minutes. The solution was drained from the resin in the reaction vessel. This washing procedure was repeated twice. DMF (2 ml) was added to the reaction vessel to keep the resin swollen.

Step 6. Fmoc-glycine (Fmoc-Gly, 0.238 g, 0.8 mmol), HOBt (108 mg; 0.8 mmol) and DIC (128 μl; 0.8 mmol) were added to a 10 ml-test tube containing 2 ml DMF. The mixture was stirred for 10 minutes to start the activation of amino acid. The solution was then added to the resin which originally was placed in the reaction vessel. The resulting mixture was stirred for 1.5 hours or until a negative ninhydrin test was obtained. The solution was then drained from the reaction vessel.

Step 7. DMF (8 ml) was added to the reaction vessel. The resulting solution was vigorously stirred for 2 minutes. The solution was then drained from the reaction vessel. The washing procedure was repeated twice.

Steps 4 through 7 were then repeated employing the following order of amino acid:

Fmoc-Cys(Acm)
Fmoc-Ser(t-Bu)
Fmoc-Gly
Fmoc-Glu(O-tBu)
Fmoc-Val
Fmoc-Ser(t-Bu)
Fmoc-Arg(Pmc)
Fmoc-Cys(Acm)
Fmoc-Gln
Fmoc-Val
Fmoc-Ile
Fmoc-Arg(Pmc)
Fmoc-Leu After completion of the synthesis of the desired peptide-resin, the reaction vessel containing the peptide-resin was then placed in a desiccator and dried overnight under vacuum. The yield of peptide-resin was 0.635 g. The dried peptide-resin was removed from the reaction vessel and placed in a 50 ml round-bottom flask containing a magnetic stirring bar. The cleavage of the peptide from the resin with TFA was carried out with the following procedure: A scavenger solution, containing 0.75 g phenol, 0.5 ml $H_2O$, 0.5 ml thioanisole, and 0.25 ml ethanedithio, was added to the round-bottom flask. The resulting mixture was stirred for 5 minutes. 10 ml TFA was added drop by drop into the flask while kept stirring vigorously. The resulting mixture was stirred for 2.5 hours at room temperature.

The mixture was filtered through a medium-porosity filter, fritted glass funnel. The TFA-peptide solution was sucked into another 500 ml round-bottom flask containing 200 mL cold diethyl ether by applying vacuum. Peptide was allowed to be precipitated in the ether solution at 4° C. overnight, then collected by filtering the mixture through a fine-porosity, fritted glass funnel. The peptide pellet on the filter was washed with cold ether (10 ml×3) to remove the scavenger. The peptide pellet was then dissolved with 25% aqueous acetic acid and then lyophilized to yield the crude peptide (about 400 mg dry weight, purity ~80%).

The crude peptide was purified by reversed-phase high performance liquid chromatography (RP-HPLC). Purification was carried out on a preparative 21.2×250 mm Supelcosil PLC-18 (octadecyl, $C_{18}$) column(120 Angstrom pore size, 12 μm particle size, 190 $m^2$/g surface area; Supelco, Bellefonte, Pa., U.S.A) at 5.0 ml/min flow rate at room temperature. A linear gradient program was utilized, where solvent A was water with 0.1% TFA, and solvent B was acetonitrile-water (50/50: v/v, containing 0.1% TFA). The gradient was developed from 20 to 100% over 80 min. Separation profiles were recorded and analysed using a Perkin-Elmer LC-100 integrator. The desired peptide component was eluted and collected with the Pharmacia Model FRAC-100 automatic fraction collector (Uppsala, Sweden). The fractions of identical component were combined and lyophilized. The purified peptide (275 mg dry weight, purity >98%), $Cys(Acm)^{6,13}$-pentadecapeptide, was kept frozen at −20° C.

For cyclisation of the disulfide bridge of the peptides, iodine oxidation in 80% aqueous acetic acid was used to remove the cysteine-protecting groups, Acm, and furnished the intramolecular disulfide bridge simultaneously. Cys (Acm)$^{6,13}$-pentadecapeptide (275 mg 0.155 mmole) was dissolved in 50 ml 80% aqueous acetic acid. This solution was slowly added to a 250 ml round-bottom flask containing iodine (378 mg, 1.4 mmole) in 100 ml 80% aqueous acetic acid by stirring vigorously. Reaction was allowed to continue for 2 hours at room temperature and terminated by adding the ascorbic acid (Vitamin C) to the resulting solution. Liquid volume was then reduced by rotary evaporation and peptide recovered by lyophilization. The cyclised peptide was then purified by RP-HPLC as described in the purification of linear peptide. After lyophilization, 165 mg cyclic pentadecapeptide with 96% purity was yielded. The total yield of synthesis was about 46%.

B. Synthesis of pentadecapeptide (Ref No. 9404): (SEQ ID NO: 7)

Leu$^1$-Arg-Ile-Val-Gln-Cys-Arg-Ser-Val-Glu-Gly-Ser-Cys-Gly-Phe$^{15}$CONH$_2$ (cyclic disulfide)

The procedure set forth in EXAMPLE A was employed. The modification consisted of omitting Wang resin and replacing it with the Rink amide resin.

C. syntliesis of the pentadecapeptide (Ref No. 9410): (SEQ ID NO: 12)

H-Leu$^1$-Arg-Ile-Val-Gln-Cys-Arg-Ser-Val-Glu-Gly-Ser-Cys-Gly-Phe$^{15}$ (cyclic disulfide)

The procedure set forth in EXAMPLE A was employed. The modification consisted of the replacement of Fmoc-Leu and with 4methyl-pentacarboxylic acid, resulting in the synthesis of the desamino pentadecapepude.

D. Synthesis of the pentadecapeptide (Ref No. 9405): (SEQ ID NO: 8)

Ch$_3$CO-Leu$^1$-Arg-Ile-Val-Gln-Cys-Arg-Ser-Val-Glu-Gly-Ser-Cys-Gly-Phe$^{15}$ (cyclic disulfide) (SEQ ID NO: 8)

The procedure set forth in EXAMPLE A was employed. After completion of the synthesis of the desired deblocked peptide-resin, 5 ml solution of 20% acetic anhydride in DMF was added. After 5 minutes, 71 μl (0.4 mmols) of diisopropylethylamine (DIEA) was added to neutralize the protons that were generated. Acetylation of the peptide was performed at room temperature for 30 minutes. The peptide-resin was washed twice with DMF and twice with DCM and the N-acetyl peptide resin was ready for TFA cleavage as shown in EXAMPLE A.

E. Synthesis of the dicyclo-pentadecapeptide (Ref No. 9408): (SEQ ID NO: 11)

Leu$^1$-Arg-Ile-Val-Gln-Cys-Lys-Ser-Val-Glu-Gly-Ser-Cys-Gly-Phe$^{15}$ (cyclic disulfide)

The following procedure was employed in preparing the pentadecapeptide:

Step 1. Boc-L-phenylalanine-PAM resin (0.400 g, 0.2 mmol; Auspep, Melbourne, Australia; Cat#5290F, Batch#494123) was placed in a 10 ml reaction vessel. The resin was washed with DCM (4 ml) by vigorous stirring for 2 minutes. The DCM solution was then drained from the reaction vessel. This washing was repeated once.

Step 2. 50% TFA/DCM solution (4 ml) was added to the reaction vessel. The resulting mixture was stirred for 2 minutes. The solution was then drained from the reaction vessel. This deprotection procedure was repeated once with a stirring time of 18 minutes. The solution was drained from the reaction vessel. DCM (4 ml) was added to the reaction vessel and the content was allowed to stand for 2 minutes. The solution was again drained from the resin. This washing procedure was repeated twice. 10% DIEA/DMF (4ml) was added to the reaction vessel. The resulting mixture was allowed to stand for 1 minute and the solution removed as before. This deprotection procedure was repeated once. DMF (4ml) was added to the resin complex in the reaction vessel. The resulting solution was allowed to stand for 2 minutes, followed by the removal of the solution from the vessel. This washing procedure was repeated four times. Finally, DMF (2 ml) was added to the reaction vessel to keep the resin swollen.

Step 3. Fmoc-glycine (Fmoc-Gly, 0.238 g, 0.8 mmol), HOBt (108 mg; 0.8 mmol) and DIC (128 μl; 0.8 mmol) were added to a 10 ml-test tube containing 2 ml DMF. The mixture was stirred for 10 minutes to activate the amino acid. The solution was then added to the resin in the reaction vessel. The resulting mixture was stirred for 1.5 hours or until a negative ninhydrin test was obtained. The solution was then drained from the reaction vessel.

Step 4. DMF (8 ml) was added to the reaction vessel. The resulting solution was vigorously stirred for 2 minutes, followed by the removal of the supernatant. The washing procedure was repeated twice.

Step 5. 25% piperidine/DMF solution (4 ml) was added to the reaction vessel. The resulting mixture was stirred for 2 minutes. The solution was drained from the reaction vessel. This deprotection procedure was repeated once with stirring for 18 minutes. The solution was drained from the reaction vessel.

Step 6. DMF (8 ml) was added to the reaction vessel. The resulting solution was stirred for 2 minutes. The solution was drained from the reaction vessel resin. This washing procedure was repeated twice. 2 ml DMF was added to the reaction vessel to keep the resin swollen.

Steps 3 through 6 were then repeated with the following order of amino acids:
Fmoc-Cys(Acm)
Fmoc-Ser(Bzl)
Fmoc-Gly
Fmoc-Glu(O-tBu)
Fmoc-Val
Fmoc-Ser(Bzl)

Step 7. Steps 3 and 4 were repeated to couple Fmoc-Lys (Boc) to Ser in the position 184. After completion of coupling, the reaction vessel containing the peptide-resin was then placed in a desiccator and dried overnight under vacuum. The peptide-resin was then transferred to a 10ml-reaction vessel. DCM (4 ml) was added to the reaction vessel. The resin was washed with vigorous stirring for 2 minutes. The DCM solution was then drained from the reaction vessel. This washing was repeated once.

Step 8. Step 2 was used to remove the Boc group and the t-Bu group from the side chain of lysine and glutamic acid, respectively.

Step 9 1 ml of 1.5% DIEA/DMF was added to the reaction vessel. Benzotriazo-1-yl-oxy-tris-(dimethylamino) phosphoniumhexafluorophosphate (BOP) (400 mg; 0.90 mmol), HOBt (122 mg, 0.90 mmol), and DIEA (400 μl, 2.25 mmol) were dissolved in 3.4 ml of 1.5% DIEA/DMF and then added to the reaction vessel. The resulting mixture was stirred for 3 hours or until a negative ninhydrin test was obtained before the removal of the supernatant from the reaction vessel. DMF (8 ml) was then added to the reaction vessel. The resulting solution was vigorously stirred for 2 minutes. The solution was then drained from the reaction vessel. The washing procedure was repeated twice.

Step 10. Steps 5 through 6 were then repeated to remove the Fmoc group from the α-amino group of the lysine residue in the peptide-resin.

Steps 3 through 6 were then repeated with the following order of amino acids:

Fmoc-Cys(Acm)
Fmoc-Gln
Fmoc-Val
Fmoc-Ile
Fmoc-Arg(Pmc)
Fmoc-Leu

After completion of the synthesis of the desired peptide resin, Step 4 was then repeated to remove the Fmoc group from Leu and get the deblocked peptide resin. The reaction vessel containing the peptide resin was then placed in a desiccator and dried overnight under vacuum. 604 mg peptide-resin was yielded. The dried peptide resin was removed from the reaction vessel and placed in a 25 ml round-bottom flask containing a magnetic stirring bar. Trifluoromethanesulfonic acid (TFMSA)/TFA cleavage protocol was used to cleave peptide from the PAM resin: A scavenger solution, containing 500 μl thioanisole, and 250 μl ethanedithio, was added to the flask. The resulting mixture was stirred for 10 minutes at room temperature. 5 ml of TFA was added drop by drop into the flask while kept stirring vigorously. The resulting mixture was stirred at room temperature for 15 minutes. Place the flask in an ice-bath and then 500 ml of TFMSA was slowed added while kept stirring vigorously. The resulting mixture was stirred in the ice-bath for 10 minutes and at room temperature another 15 minutes. Cold diethyl ether (50 ml) was added to the flask to stop the reaction and precipitate the cleaved peptide. The peptide was collected by filtering the mixture through a fine-porosity, fritted glass funnel and washed with cold ether (10 mL×3) to remove the scavenger. The peptide pellet was dissolved with 30 ml of 50% acetonitrile/$H_2O$ followed by the addition of 5 ml of cold 10% $NH_4HCO_3$ to neutralize the solution. The crude peptide (519 mg, purity ~69%) was obtained after lyophilization.

The preparation of peptide with cyclic disulfide form and the purification of pure final product are shown in EXAMPLE A.

F. Synthesis of the hexadecapeptide (Ref No. 9604)

Tyr-Leu-Arg-Ile-Val-Gln-Cys-Arg-Ser-Val-Glu-Gly-Ser-Cys-Gly-Phe (cyclic disulfide) (SEQ ID NO: 19)

The procedure set forth in Example A was employed, modified by the addition of a further repetition of the steps 4 to 7 using Fmoc-Tyr(t-Bu).

Cumulative Weight Gain and Food Consumption.

Cumulative weight gain and food consumption were determined at 3-day intervals by the measurements of body weight and uneaten food remaining in the cages. The animals were placed in a covered chamber to minimise movement during the weighing procedure. The food consumption data were obtained by subtracting the amount of uneaten food remaining in the cages from the original provision.

Assays for Plasma Triglyceride and Total Cholesterol.

The animals were anaesthetised with sodium pentobarbitone (80 mg/kg body weight) 12 hr after the last dose of hGH 177–191. Blood samples were collected from the tail vein of anaesthetised animals 45 mins after the administration of anaesthetic. After being centrifuged at 2000×g for 5 minutes, plasma was removed from the samples and used for metabolite assays. Triglyceride and total cholesterol in plasma were measured by enzyme-spectrophotometric methods. The reagents are based on either a modified glycerol phosphate oxidase (GPO)-Trinder's type colour reaction[24] or a cholesterol oxidase-4-aminoantipyrine method[25]. All assays were performed with the CentrifiChem System 400 (Union Carbide) containing an automated pipetter, a centrifugal analyser and a recording spectrophotometer. Seronorm Lipid (Nycomed Pharma Co., Oslo, Norway) was used as the calibrator.

Determination of Adipose Tissue Weight

The procedure for the isolation and measurement of intact epididymal fat pads was established in previous studies of epididymal growth of GH-deficient (lit/lit) mice. In the present study, white adipose tissues, either whole epididymal or parametrical fat pads, were excised with the identical techniques as previously described[22] from the mice immediately after sacrifice. The tissues were washed in cold physiological saline, blotted and weighed. For ex vivo lipogenic assays, the portions of adipose tissues without blood vessels were used.

Hormone-sensitive Lipase (HSL) Assay

Hormone-sensitive lipase (HSL) activity of isolated adipocytes was used as a model to evaluate the lipolytic effect of hGH 177–191 peptide and analogues. In this assay $[C^{14}]$-triolein was used as a substrate by HSL. The amount of hydrolyzed $[C^{14}]$-oleic acid was determined and used as an index of HSL activity.

The adipocytes were prepared from the epididymal fat pads of male Zucker fatty (fa/fa) rats by collagenase digestion. Fat pads (5 g) were finely-cut into small (2–3 mm) pieces and placed in a siliconised glass vial containing 10 ml digestion medium. The digestion medium contained microbial collagenase (Type II) at a concentration of 1 mg/ml in Krebs-Ringer phosphate buffer (pH 7.4) at half $Ca^{2+}$ strength, at 2% (w/v) of bovine serum albumin (BSA Fraction V). After digestion at 37° C. for 1 hr under an atmosphere of 95% $O_2$/5% $CO_2$, adipocytes were liberated from any remaining pieces of adipose tissue by gently sucking the suspension up and down with a 5.0 ml pipette with the tip opening of 3–4 mm. The adipocytes released from tissue were then filtered through nylon chiffon into a siliconised glass tube and washed twice with 6 ml of collagen free albumin buffer. The isolated adipocytes were resuspended with 10 ml collagen-free buffer and the concentration of adipocytes was estimated by counting an aliquot of a predetermined volume of cells on a microscope slide. It normally gave approximate $10^9$ cells/ml of adipocytes in Krebs-Ringer phosphate buffer (pH 7.4).

The HSL activity was measured at 37° C. for 1 hour in a final volume of 200 μl, containing 10 μmoles phosphate buffer (pH 7.0). 15 μmoles of emulsified $[C^{14}]$-triolein, and $10^8$ cells. The substrate, $[C^{14}]$-triolein, was pre-emulsified with un-labelled triolein to provide the final emulsion contains 15 μmoles of triolein and 375,000 cpm in 0.1 ml. Different concentrations of hGH 177–191 peptide or analogues were added to evaluate their effects on the HSL activities. The reaction was stopped by adding 1 ml of the fatty acid extraction mixture of choloform-methanol-benzene 2:2:4:1 containing 50 μl oleic acid, followed by adding 67 μl of 0.5N NaOH. To extract and isolate free fatty acid, samples were vortexed for 20 seconds and then centrifuged at 1,000×g for 5 minutes. A 200 μl portion of the alkaline aqueous upper phase containing fatty acids was transferred to scitillation vials. The $[C^{14}]$-radioactivity was measured by a liquid scintillation counter. The remaining cell suspension was assayed for protein content. The HSL activity was expressed as U/mg protein, where the release of 1 nmole of oleic acid per hour was defined as 1 U of enzyme activity.

Acetyl-CoA Carboxylase Assay

Acetyl-CoA carboxylase catalyzes the critical step in fatty acid synthesis. The acetyl-CoA carboxylase activities of both isolated adipocytes and hepatocytes in the presence of hGH 177–191 peptide or analogues were measured for the evaluation of the anti-lipogenic effect of the peptides. The acetyl-CoA carboxylase activity was determined by the $[C^{14}]$-bicarbonate fixation reaction—the rate of incorporation of acetyl-CoA dependent $H[C^{14}]O_3$ into $[C^{14}]$-malonyl-CoA.

Adipocytes were prepared with the method described in the HSL assay. Hepatocytes were prepared from the livers of male Wistar rats by collagenase digestion. The liver was finely-cut with scissors and transferred to a 250 ml Erlenmeyer flask containing 30 ml of digestion medium. The digestion medium contained microbial collagenase (Type IV) at a concentration of 30 mg/ml in calcium-free Krebs-Ringer phosphate buffer (pH 7.4) and glucose (5 mM). After digestion for 15 minutes at 37° C. under an atmosphere of 95% $O_2$/5% $CO_2$ the hepatocytes liberated from the tissue were then filtered through nylon chiffon into a siliconised glass tube and washed twice with fresh collagen-free digestion medium. The isolated cells were resuspended in 45 ml of medium containing extra EDTA (0.45 mmoles), gelafine (0.7 ml), 2-{[tris(hydroxymethyl)methyl]amino}ethane sulphonic acid (TES) (0.9 mmoles), and gassed with 95% $O_2$/5% $CO_2$ prior to use.

The isolated cells were first preincubated at 37° C. for 30 minutes in a mixture containing 50 mM Tris-HCl buffer (pH 7.5), 10 mM potassium citrate, 10 mM $MgCl_2$, 1 mM dithiothreitol (DTT), and BSA (0.8 mg/ml). The reaction was then initiated by the adding an aliquot of the preincubated cells to an assay mixture (final volume, 500 μl) containing 50 mM Tris-HCl buffer (pH 7.5), 10 mM potassium citrate, 10 mM $MgCl_2$, 1 mM dithiothreitol (DTT), BSA (0.8 mg/ml), 3.75 mM ATP, 0.125 mM acetyl-CoA, and 12.5 mM $NaH[C^{14}]O_3$ (0.44 μCi/μmol). After incubation at 37° C. for 10 minutes, the reaction was terminated with 0.1 ml of 6M HCl. The reaction mixture was then allowed to stand in a vacuum desiccator for 30 minutes to remove the unreacted $NaH[C^{14}]O_3$ and followed by centrifugation at 1500 g for 10 minutes to eliminate the insoluble material. A 0.5 ml aliquot of the supernatant was taken and transferred to scintillation vials. The $[C^{14}]$ radioactivity was measured with a liquid scintillation counter. The remaining cell suspention was assayed for protein content. Specific activity of the enzyme was expressed as mU/g cell dry weight, where 1 U of acetyl-CoA carboxylase was defined as that amount which catalyzed the carboxylation of 1 μmole acetyl-CoA per minute.

Assay for Lipolytic Activity

The lipolytic action of hGH 177–191 and analogues on the isolated adipose tissues was demonstrated by the release of glycerol and free fatty acid (FFA) into the medium during incubation at 37° C.

Adipose tissues were removed from animals and sliced into segments of approximately 200 mg each. Then the tissues were pre-incubated in 25 ml vials containing 2 ml of Krebs-Ringerbicarbonate (KRB) buffer, 4% defatted BSA and 5.5 mM glucose under an atmosphere of carbogen (95%$O_2$/ 5%$CO_2$) at 37° C. for 1 hour. Tissues were then transferred to another vials with fresh medium and the incubation was initiated by adding hGH 177–191 peptide or analogues into the vials. The mixtures were then incubated at 37° C. for 90 minutes. After incubation, the tissues wee removed and aliquots (200 μl) of samples withdrawn from the medium were assayed for the contents of glycerol or free fatty acid (FFA) either by the enzyme assay (glycerol kinase) or calorimetric (copper-dye) spectrometry. The NADH or color produced was then monitored by the absorption at 340 nm and 610 nm, respectively.

Assay for Oxidation of Free Fatty Acid

The effect of hGH 177–191 or analogues on the free fatty acid (FFA) oxidation in the adipose tissues is evaluated by the measure of converted $[C^{14}]O_2$ from $C^{14}$-palmitic acid. The $[C^{14}]O_2$ a final product of FFA oxidation, was trapped by hyamine hydroxide and measured by liquid scintillation counter. The rate of FFA oxidation was then determined by $[C^{14}]$ radioactivity.

Adipose tissues removed from laboratory animals were sliced into segments of approximately 200 mg each. The tissues in 25 ml vials containing 2 ml of Krebs-Ringer phosphate (KRP) buffer, and 2% defatted bovine serum albumin (BSA) were pre-incubated at 37° C. for 30 minutes under an atmosphere of carbogen (95%$O_2$/5%$CO_2$) Then the tissues were transferred to Konte flasks with fresh incubation medium with 0.15 mM sodium $[C^{14}]$-palmitate (final $[C^{14}]$-specific activity, 0.20 μCi/μmol) and hGH 177–191 peptide or analogues (1–1000 nM). A filter paper roll was placed in a well inside of flask and then the flask was seal with rubber septum stopper. The incubation at 37° C. was lasted for 1 hour under an atmosphere of carbogen and was then terminated by injecting 250 μl of 4.5 M $H_2SO_4$ with a needle through the rubber septum into the medium of a flask and 250 μl of hyamine hydroxide was injected to the filter paper roll in the centre well. Flasks were incubated for a further 1 hour to complete the absorption of $[C^{14}]O_2$ by hyamine hydroxide. The filter paper rolls were then removed and transferred to scintillation vials. The $[C^{14}]$ radioactivity was measured with a liquid scintillation counter. The rate of $[C^{14}]$-palmitic acid oxidation to $[C^{14}]O_2$ was calculated and expressed as μmol/g tissue/hr.

Assay for Lipogenic Activity

The rate of the incorporation of exogenous $[C^{14}]$-glucose into total lipid in adipose tissue was measured as the index of anti-lipogenic activity of hGH 177–191.

Adipose tissues were sliced into segments of approximately 200 mg each and then placed in Krebs-Ringer bicarbonate (KRB) buffer (pH 7.4) containing 2% defatted BSA, and glucose (0.1 mg/ml) and gassed with 95% $O_2$–5% $CO_2$ at 37° C. After 1 hr preincubation, the tissues were transferred to another 2 ml of fresh media containing $[C^{14}]$-glucose (final specific activity 0.05 μCi/μmol), and 0.3 μM of hGH 177–191 in the presence or absence of insulin (0.1 mU/ml) for a further 90 min incubation (conditions as above). Then the tissues were removed, washed thoroughly with KRB buffer and lipid was extracted with 5 ml of chlorofom/methanol (2:1, v/v) The extraction solution was washed with 2 ml of MeOH-$H_2O$ solution containing 0.1% $MgCl_2$. A 2.5 ml aliquot of the washed extraction solution was taken and transferred to scintillation vials. The $[C^{14}]$ radioactivity was measured with a liquid scintillation counter. The rates of total lipid synthesis were expressed as μmol $[C^{14}]$-glucose incorporated into lipid/g tissue/hr.

Assays for Diacylglycerol (DAG) Rel Ase

Diacylglycerol released from isolated adipose tissue or adipocytes was quantitated using a radioenzymic assay, employing *E coli* DAG kinase and defined mixed micelle conditions to solubilize DAG and allow its quantitative conversion to $[^{33}p]$ phosphatidic acid in the presence of $[^{33}p]$-γ-ATP. Following a number of extraction steps to remove unreacted $[^{33}p]$-γ-ATP, separation of $[^{33}p]$ phosphatidic acid was achieved with the use of 1 ml Am-Prep™ minicolumns.

Statistical Analysis

The Student's t-test was used to analyse the results. All data are expressed as the mean±SEM. P values of <0.05 are accepted as statistically significant.

RESULTS

Figure 1B:
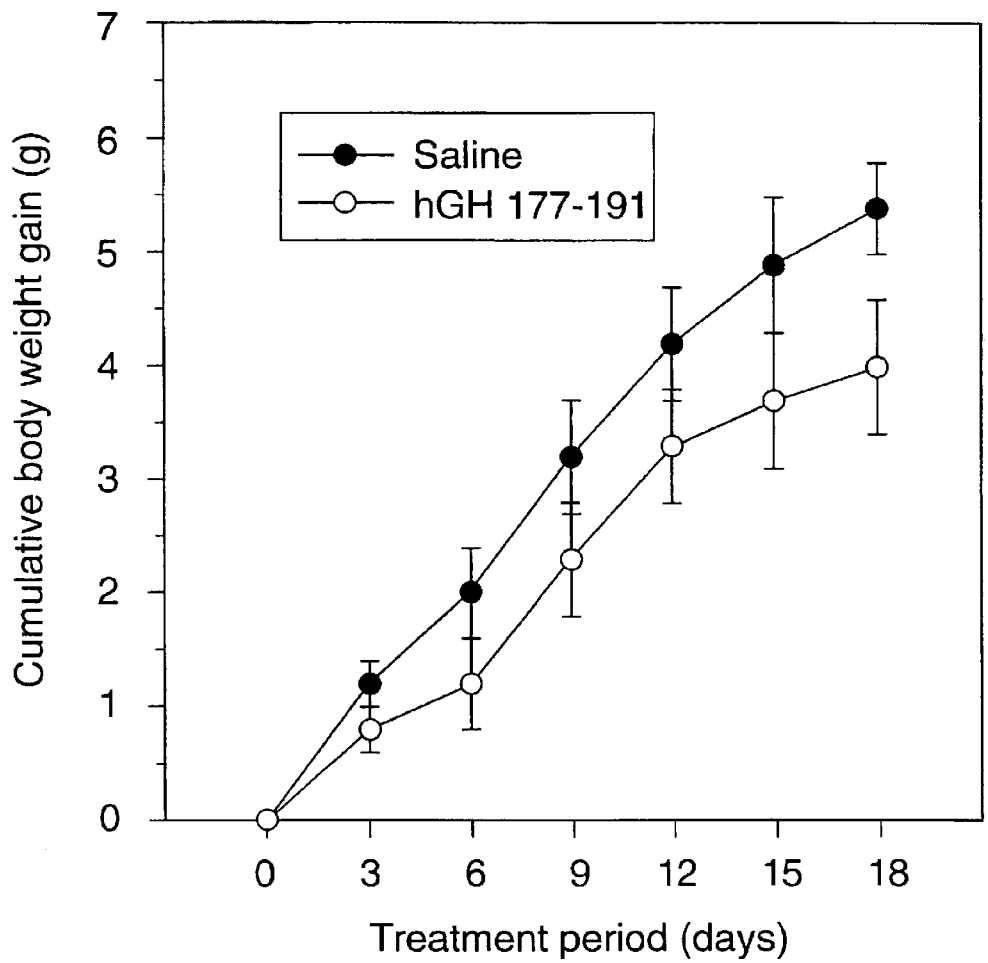
Figure 2A:
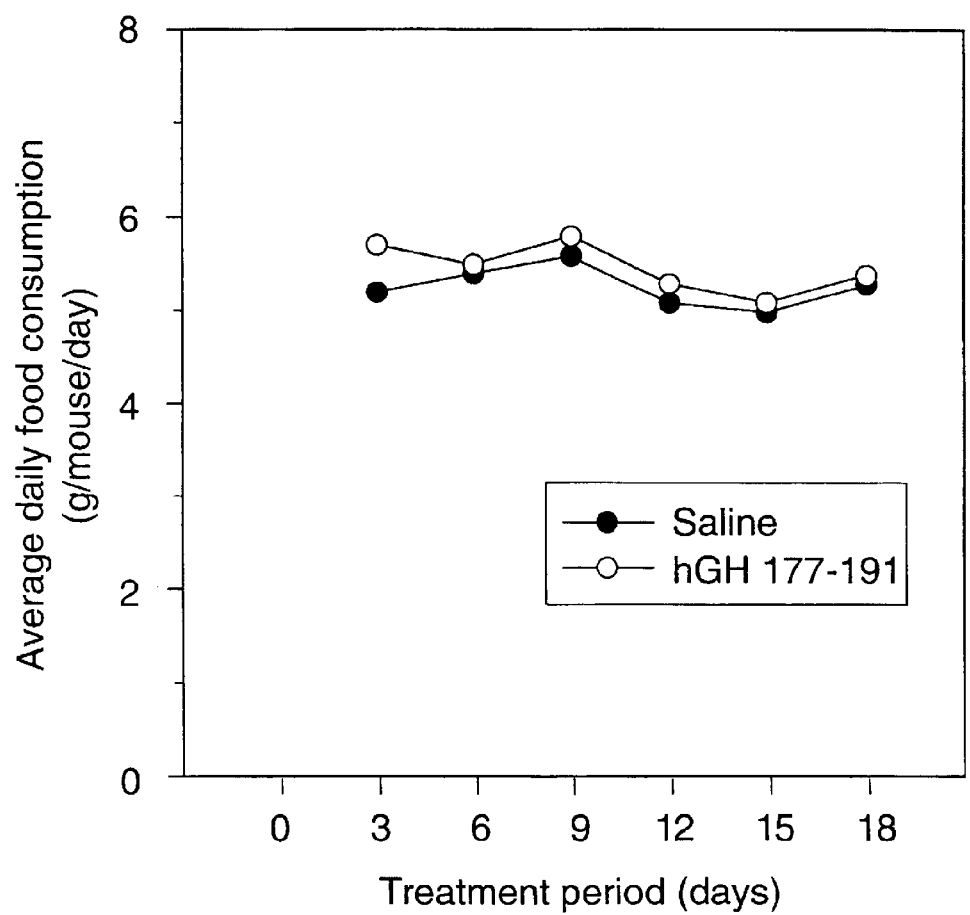
FIGS. 2A & 2B show the average daily food consumption (g/mouse/day) of C57BL/6J (ob/ob) mice during an 18day treatment period with hGH 177–191. The treatment for the four groups of animals was as described in FIGS. 1A & 1B. Each point represents the mean±SEM of 6 animals. No significance between the groups was observed at all times.
Figure 2B:
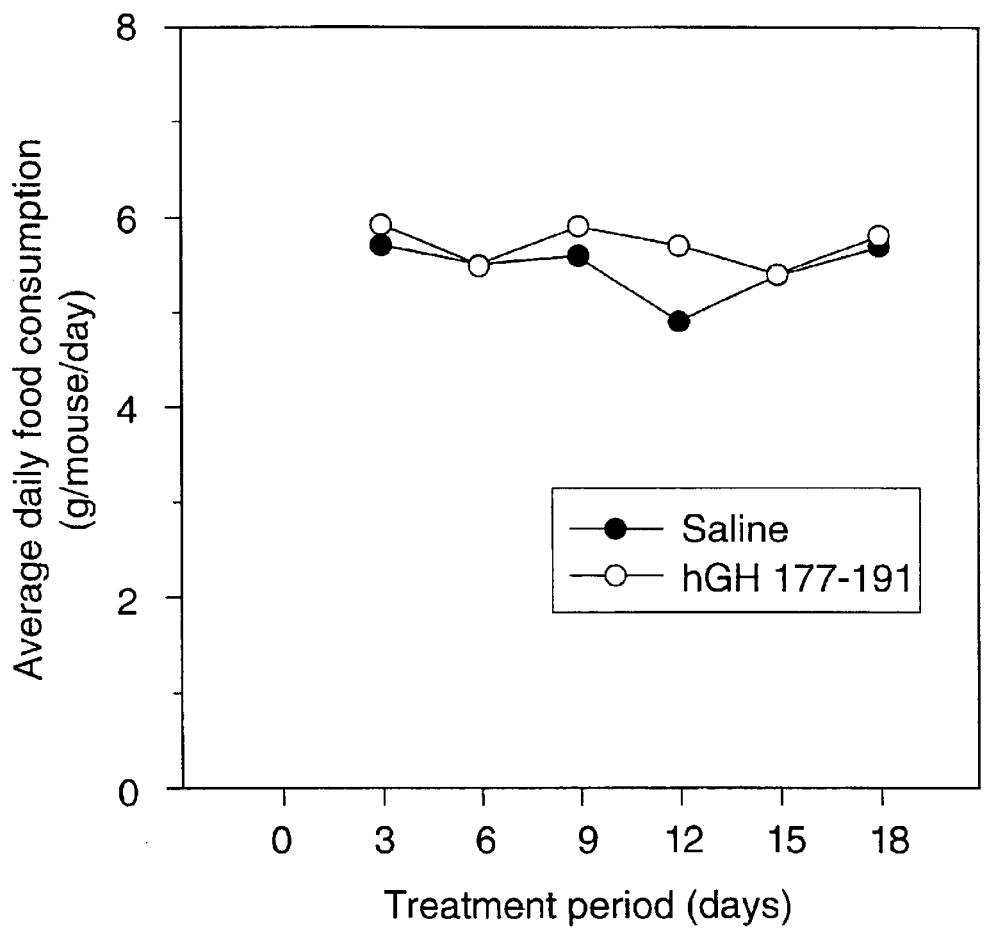
Figure 3A:
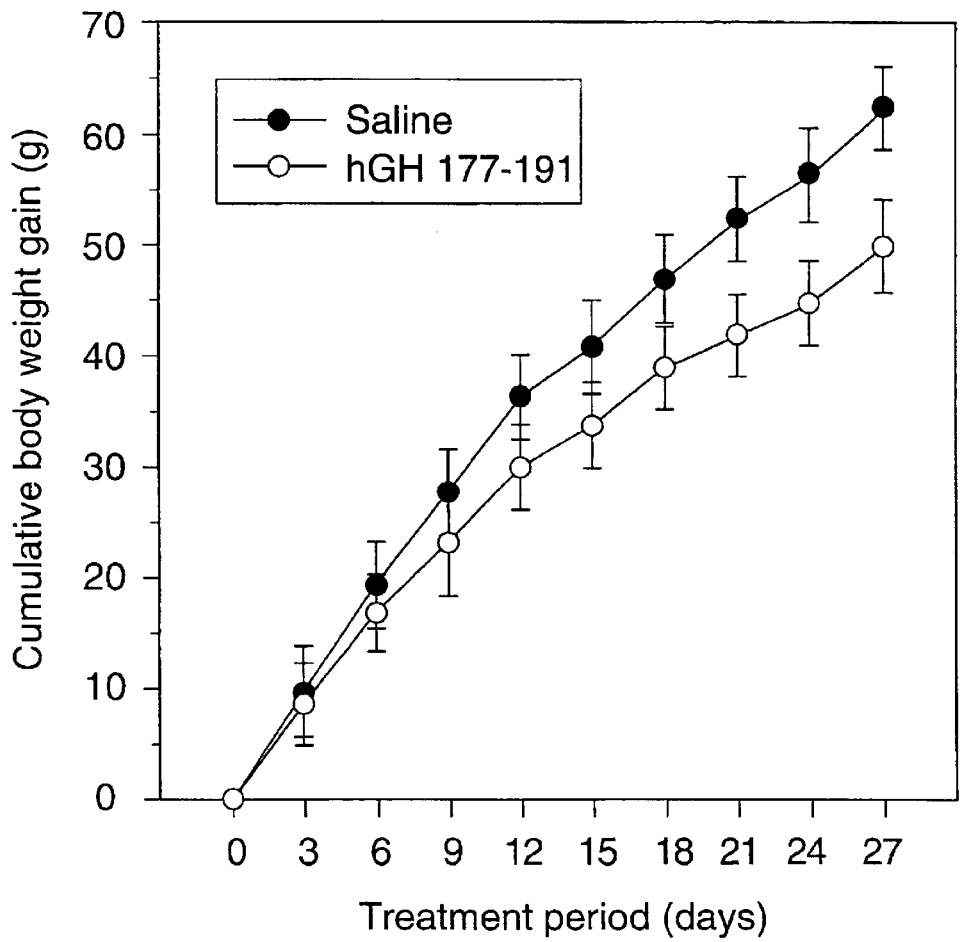
FIGS. 3A & 3B demonstrate the effect of hGH 177–191 peptide on body weight gain of 14–15 week old male Zucker fatty (fa/fa) rats during the 20 or 27-days treatment period. Animals were given a daily intraperitoneal injection of either saline or the peptide (500 µg/kg body weight) (3A) or implanted intradermally with a slow-release tablet (500 µg/day/kg body weight) in the lower quadrant of the abdomen of the animals. The control group was implanted with a placebo tablet in the same manner. Each point represents the mean±SEM of 6 animals.
Figure 3B:
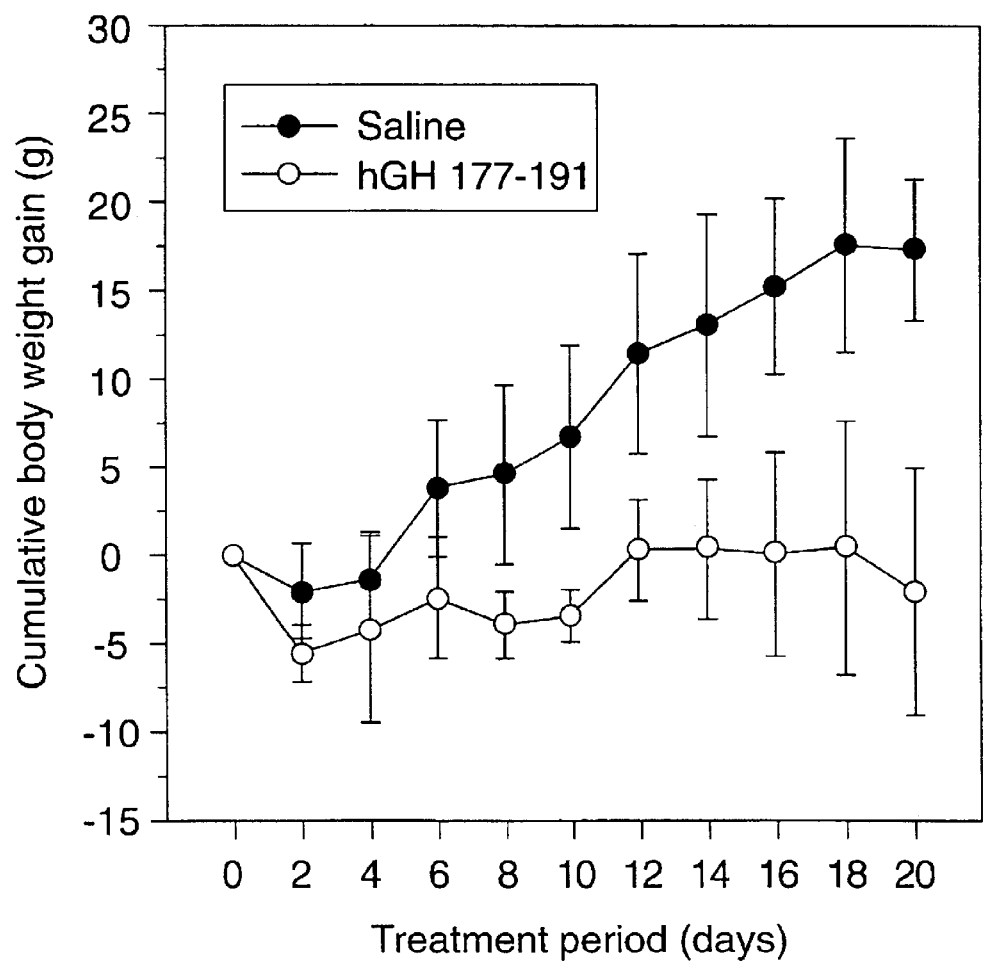
Figure 4A:
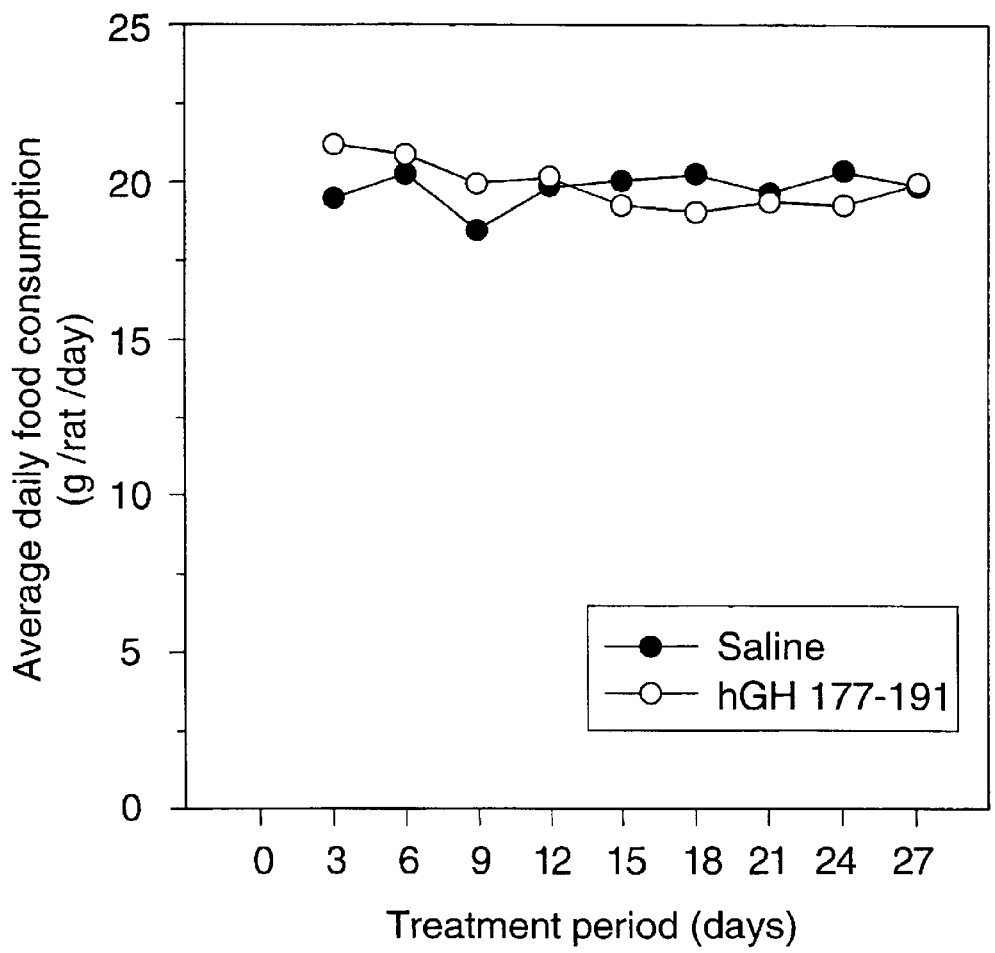
FIGS. 4A & 4B demonstrate the average daily food consumption (g/rat/day) of Zucker fatty rats during the treatment period with hGH 177–191 peptide. The treatment for the four groups of animals was as described in FIGS. 3A & 3B. Each point represents the mean±SEM of 6 animals. No significance between the test groups and the appropriate controls was observed at all times.
Figure 4B:
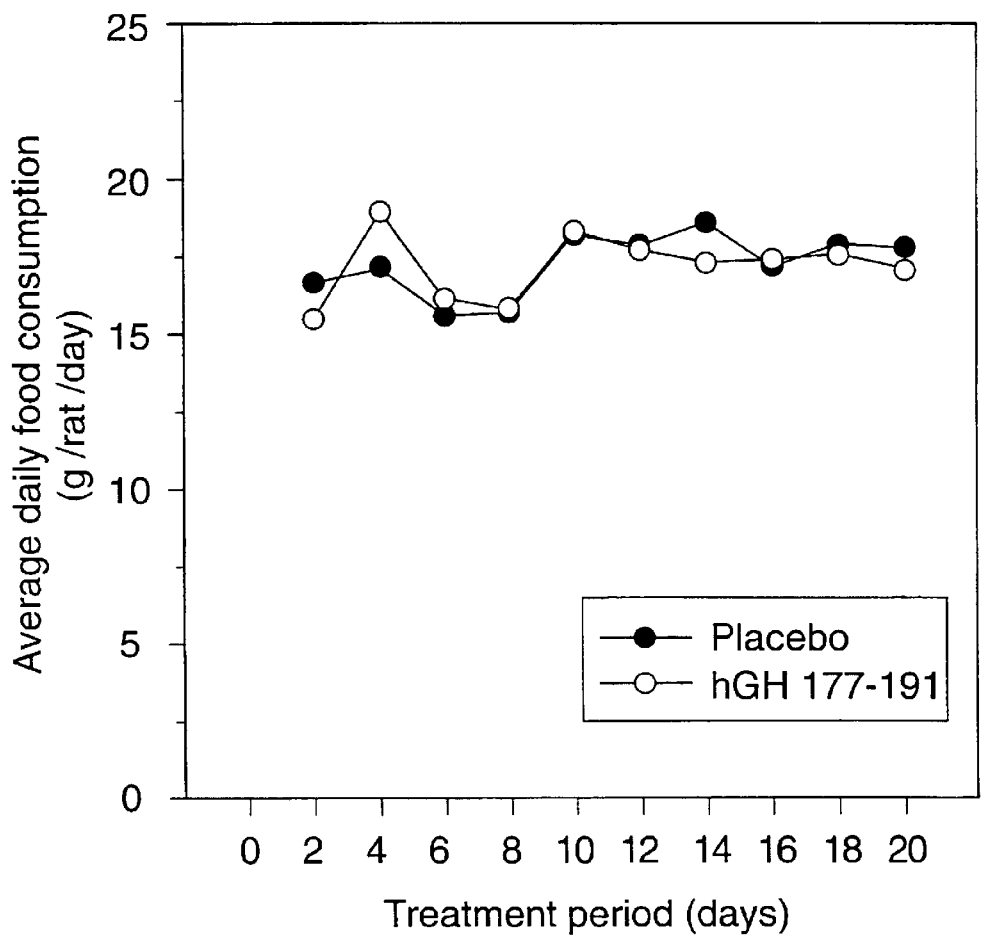
Figure 11A:
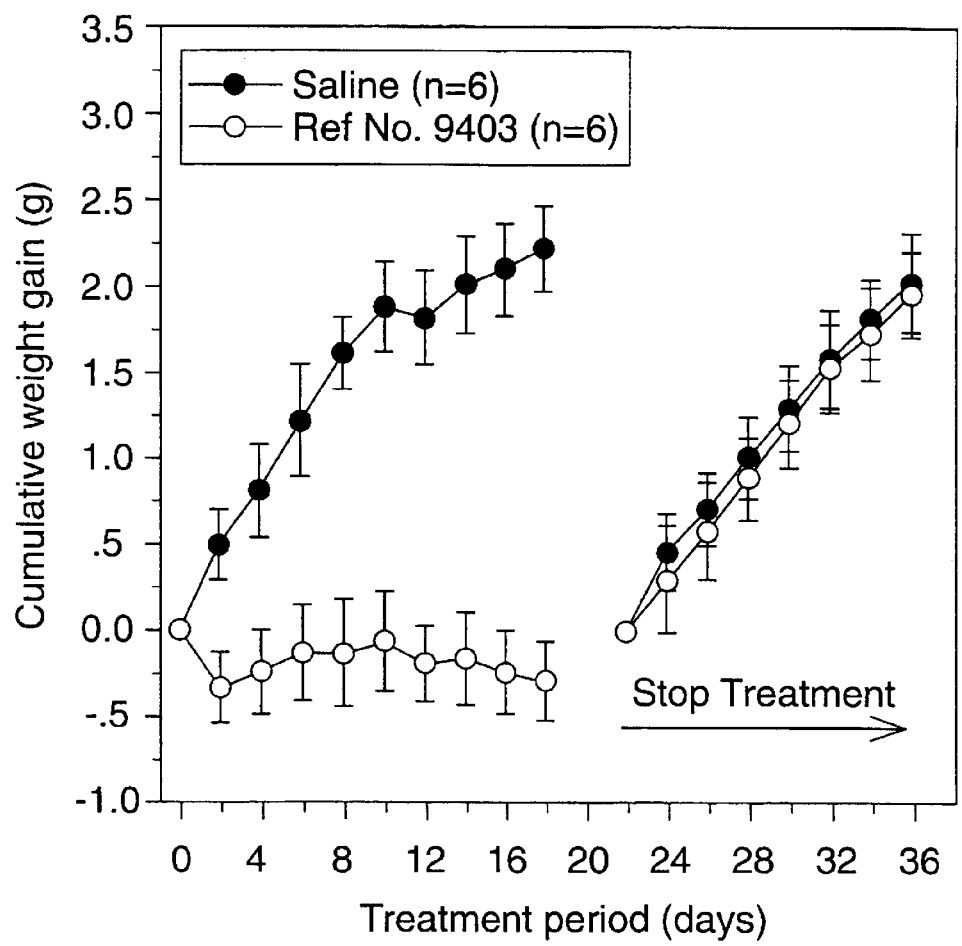
FIG. 11A demonstrates the effect of analogue Ref. No. 9403 (SEQ ID NO: 6) on body weight gain of 26-week-old C57BL/6J (ob/ob) mice during the 18 days treatment period. Animals were given a daily intraperitoneal injection of either saline (as control) or peptide analogue (500 µg/kg body weight). Each point represents the mean±SEM of 6 animals.
Figure 11B:
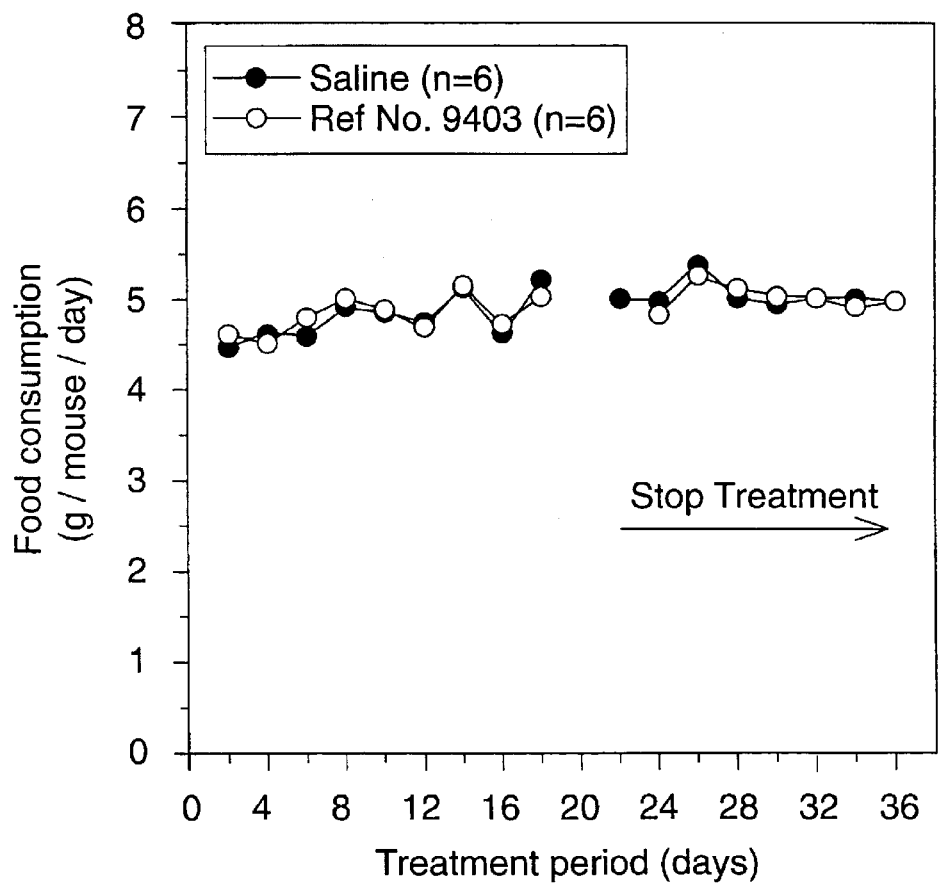
FIG. 11B shows the average daily food consumption (g/mouse/day) of 26-week-old C57BL/6J (ob/ob) mice during the treatment period with analogue Ref No. 9403 (SEQ ID NO: 6). The treatment for the two groups of animals was as described in FIG. 11A. Each point represents the mean±SEM of 6 animals. No significance between the test group and the control was observed at all times.

The chronic treatment of the obese mice and rats with the synthetic hGH 177–191 and analogues was evaluated by the measurements of a number of parameters including cumulative body weight gain and daily food consumption. During the treatment period, a clear reduction of cumulative body weight gain was observed in the hGH 177–191 treated male as well as female animals when compared with the appropriate control (FIGS. 1A, 1B). When the data were analysed and expressed as daily body weigh gain, the treated male animals reduced their body weight gain from 0.22±0.03 to 0.16±0.04 g/day and the female animals from 0.30±0.02 to 0.22±0.04 g/day. The average daily body weight gains of the both male and female treated animals showed approximately 27% lower than those of the appropriate control groups. However, no significant difference in the average daily food consumption among the 4 groups was observed (FIGS. 2A, 2B). Similar positive results have also been observed with daily oral administration at 500 µg/kg/day. These antiobesity actions of various analogues, as represented by Ref. No. 9403 (FIG. 11A) were observed in obese mice. The synthetic analogues control body weight gain without affecting the appetite of the treated animals (FIG. 11B). The similar reduction of body weight gain was found also in Zucker fatty (fa/fa) rats during hGH 177–191 treatment via either daily intraperitoneal injection or intradermal implantation of a slow-release pellet (FIGS. 3A, 3B). The food consumption of the treated Zucker rats was unchanged throughout the treatment period (FIGS. 4A, 4B). These data clearly demonstrated that the chronic treatment with hGH 177–191 peptide reduced the body weight gain without affecting food consumption.

Figure 5A:
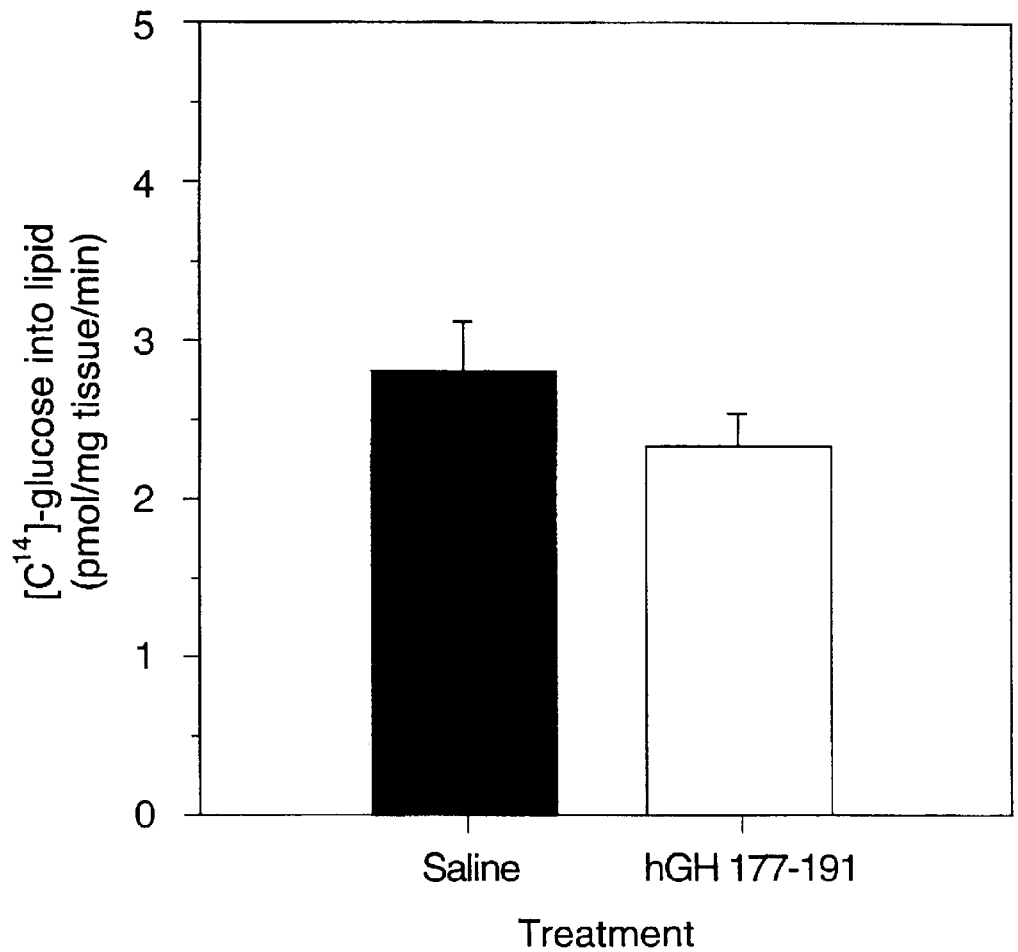
FIGS. 5A & 5B depict the ex vivo effect on lipogenesis in adipose tissues of the C57BL/6J (ob/ob) male mice (5A) and female mice (5B) after 18-day treatment with hGH 177–191. Data indicate the rate of [$C^{14}$]-lipid synthesis and are expressed as [$C^{14}$]-glucose incorporated into lipid (pmol/mg tissue/min) Values are mean±SEM of 12 determinations from 6 animals of each group. The differences between the hGH 177–191 treated and saline control groups were statistically significant.
Figure 5B:
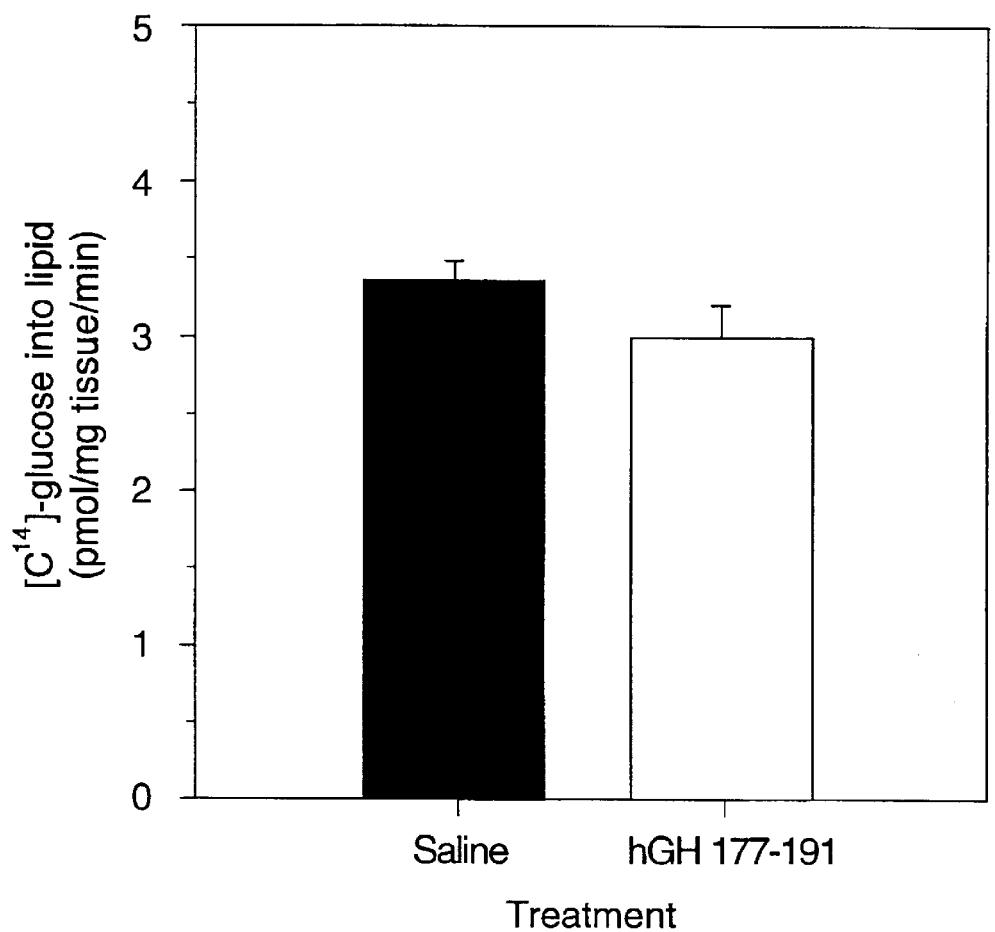
Figure 6A:
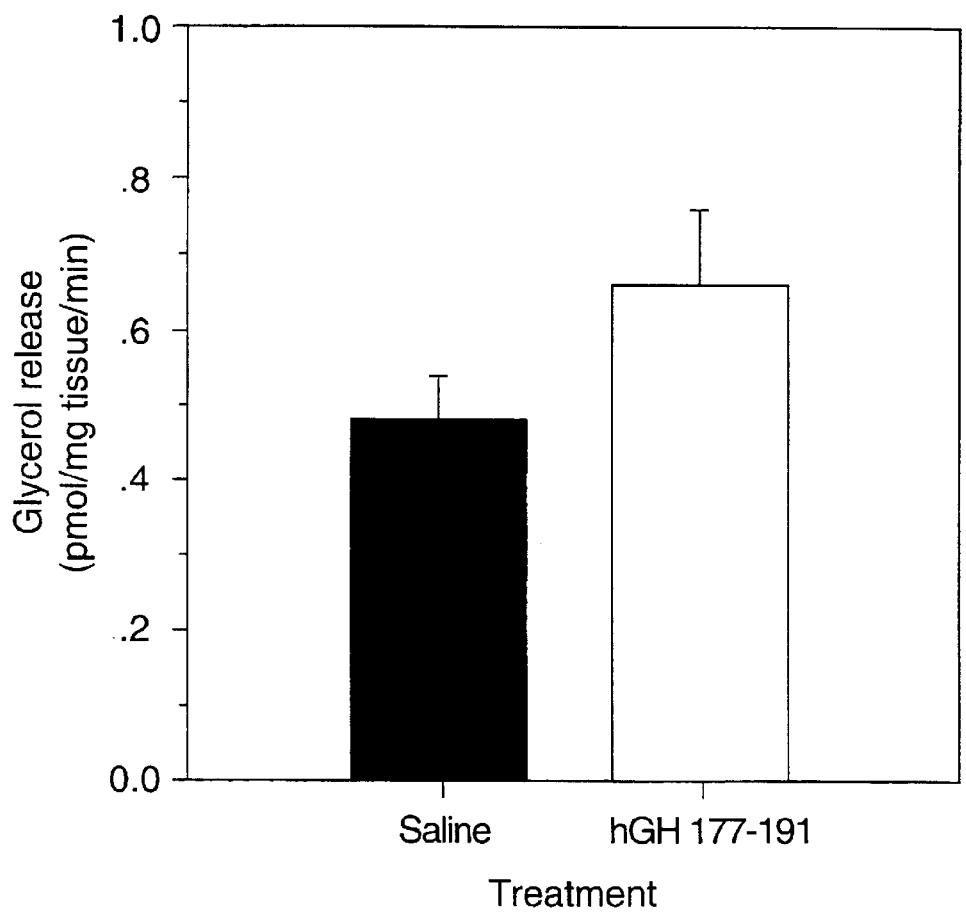
FIGS. 6A & 6B depict the ex vivo effect on lipolysis in adipose tissue of the C57BL/6J (ob/ob) male mice (6A) and female mice (6B) after 18-days treatment with hGH 177–191. Data indicate the rate of glycerol release from adipose tissues (pmol/mg tissue/min). Values are mean±SEM of 12 determinations from 6 animals of each group. The differences between the hGH 177–191 treated and saline control groups were statistically significant.
Figure 6B:
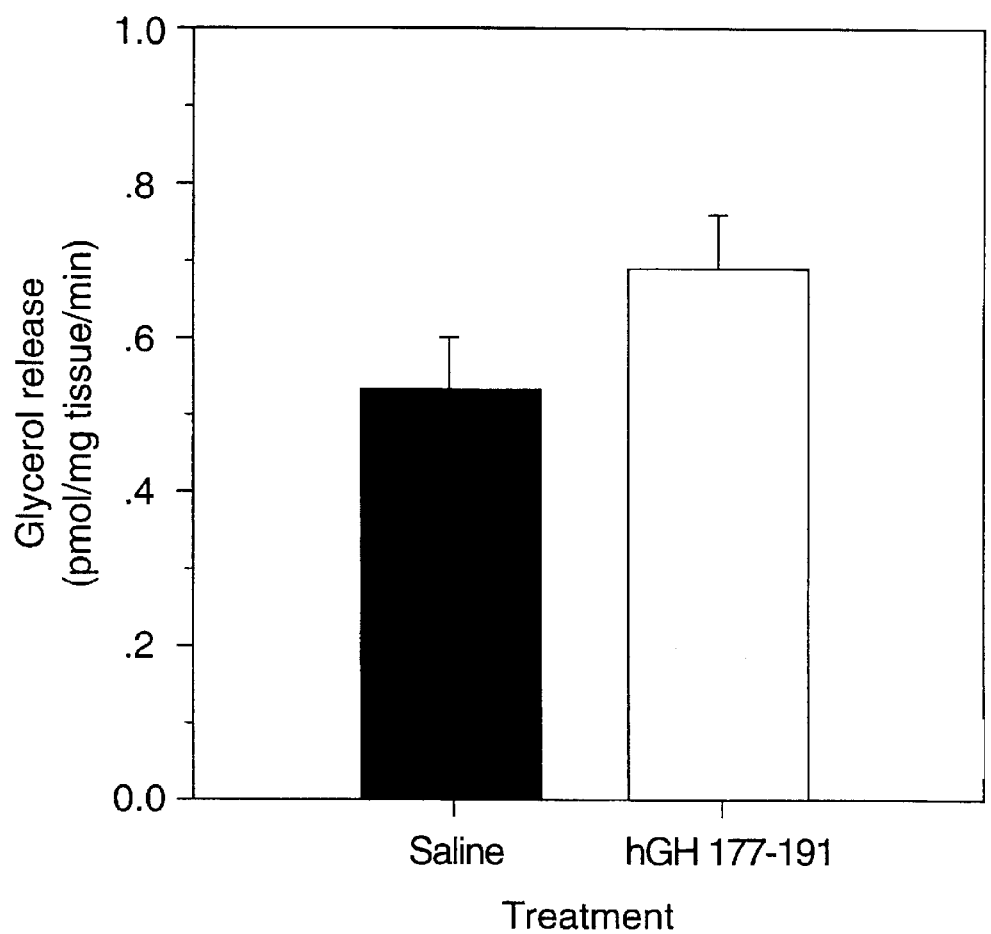

As indicated by the measurements of epididymal and parametrical fat pads, the treated mice significantly reduced their adipose tissue weights up to 20% in the males and 12% in the females as compared with the controls of the same sex (Table 1). Lipogenesis is subject to the supply of precursor metabolites such as glucose and acetate. The effect of hGH 177–191 or analogues was therefore determined by measuring the incorporation of [$^{14}$C]-glucose into lipid in isolated adipose tissues. The peptide hGH 177–191 and analogues (Table 5) reduced lipogenic activity in vitro more than 25% as compared with the control in isolated tissues from fatty Zucker rats. Decrease in lipogenesis of the adipose tissue isolated from hGH 177–191 treated mice was evident (FIGS. 5A, 5B). The tissue lipogenic activity reduced from 2.80±0.33 to 2.33±0.21 pmol/mg tissue/min in male mice and from 3.36±0.13 to 2.99±0.21 pmol/mg tissue/min in female mice. The lipolytic activity in adipose tissues of the hGH 177–191 treated obese animals was found to increase significantly in both sexes (FIGS. 6A, 6B). These results are consistent with the reduction in adipose tissue mass and cumulative body weight gain previously observed.

Figure 7:
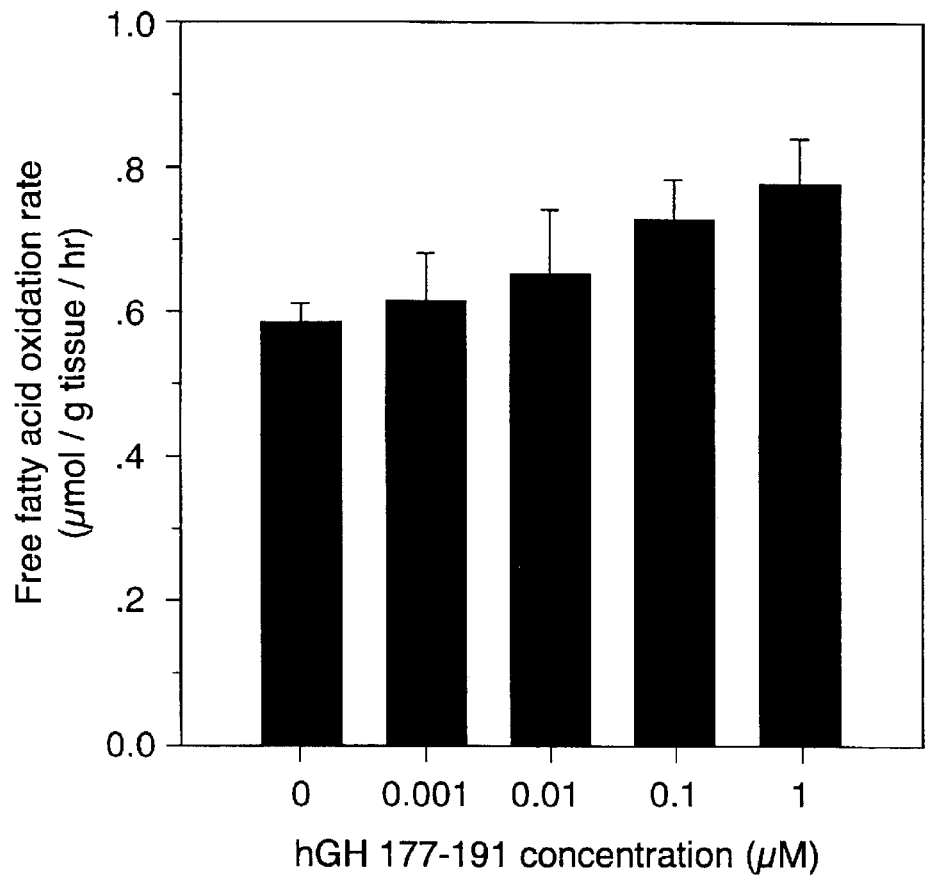
FIG. 7 illustrates the in vitro effect of hGH 177–191 on fatty acid oxidation in isolated adipose tissues of C57BL/6J (ob/ob) mice with the determination of the rate of [$C^{14}$]$O_2$ production from [$C^{14}$]-palmitic acid. The rate of [$C^{14}$]-palmitic acid oxidation was expressed as µmol/g tissue/hr.
Figure 8:
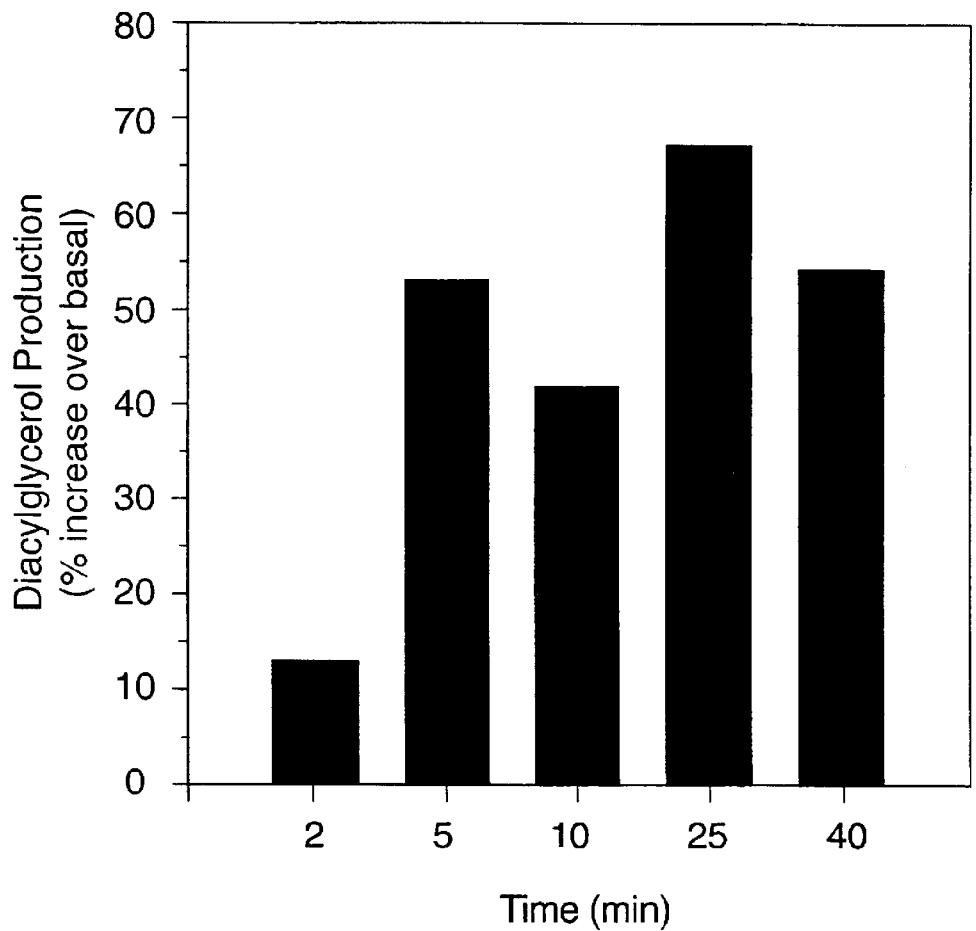
FIG. 8 illustrates the in vitro effect of hGH 177–191 on the release of diacylglycerol from isolated adipocytes of normal rats over an incubation period of 40 min. Diacylglycerol was quantitated using radioenzymic assay and the results were expressed as % increase over the basal levels.
Figure 9:
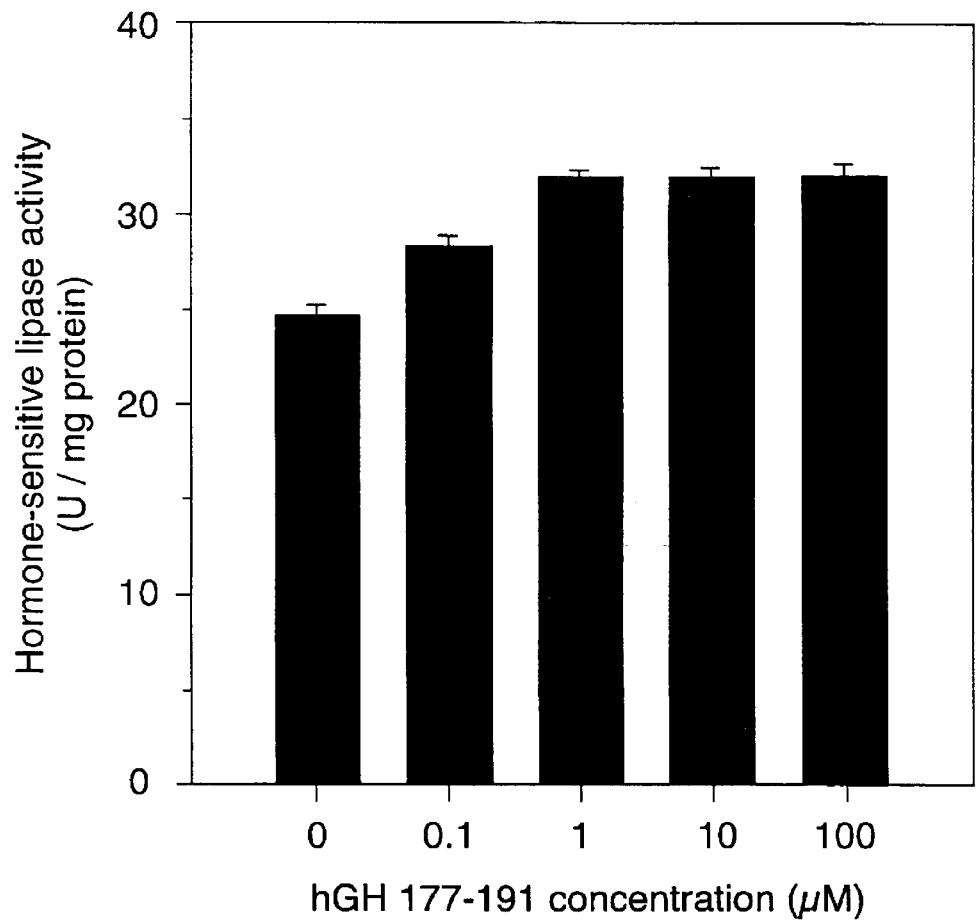
FIG. 9 shows the in vitro effect of hGH 177–191 on hormone-sensitive lipase activity in isolated adipocytes of male Zucker fatty (fa/fa) rats was determined by the amount of hydrolyzed [$C^{14}$]-oleic acid from [$C^{14}$]-triolein. The enzyme was expressed as U/mg protein, where the release of 1 nmole of oleic acid per hour was considered as 1 Unit of enzyme activity.
Figure 10A:
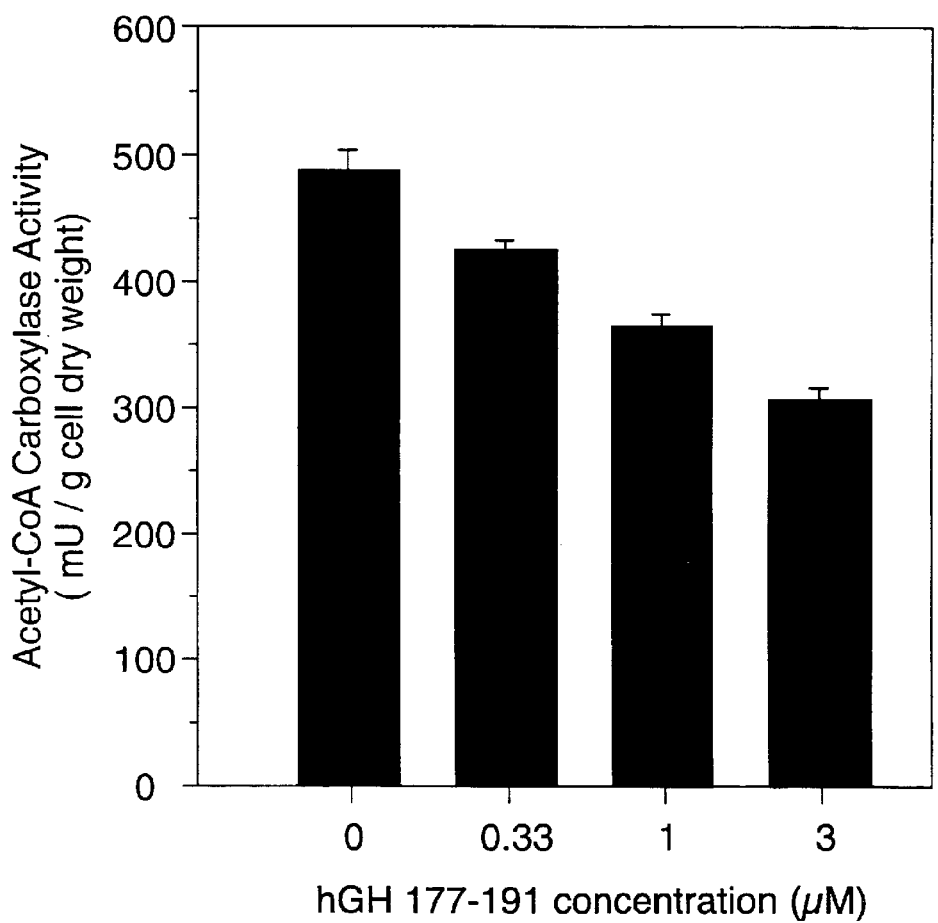
FIGS. 10A & 10B shows the in vitro effect of hGH 177–191 on acetyl-CoA carboxylase in the isolated adipocytes (10A) and hepatocytes (10B) of normal rats was determined by [$C^{14}$]-bicarbonate fixation reaction and expressed as mU/g cell dry weight, where 1 Unit of acetyl-CoA carboxylase was defined as the carboxylation of 1 µmole acetyl-CoA per minute.
Figure 10B:
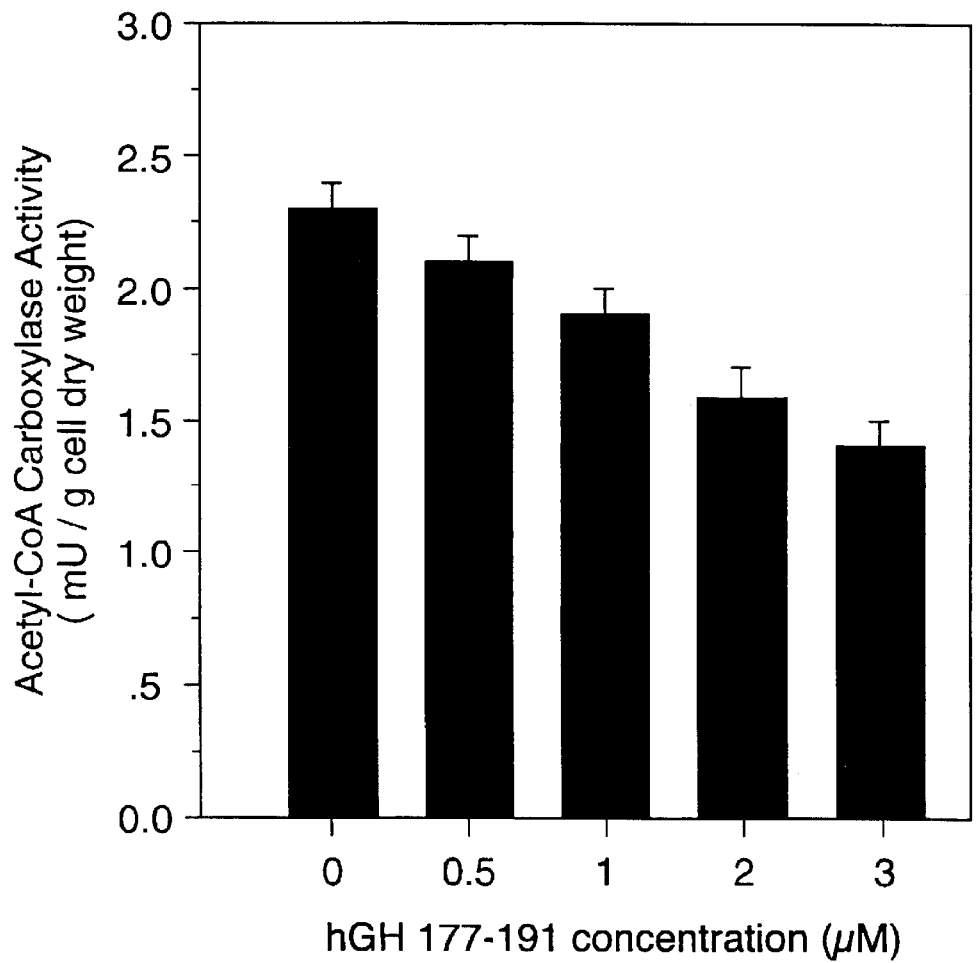

Table 2 depicts the effect of the hGH 177–191 treatment on the profiles of circulating levels of triglyceride and cholesterol. The total cholesterol in plasma was significantly reduced from 4.44±0.56 to 3.52±0.39 mmol/l in the male animals but the plasma levels of cholesterol in the treated female animals were only slightly lower than those of the control ones. On the other hand hGH 177–191 did not influence the plasma levels of triglyceride in both sexes. In the presence of hGH 177–191 and various analogues, the oxidation of fatty acids (FIG. 7) and the release of glycerol (Table 4) in adipose tissues isolated from obese animals were enhanced. This is consistent with the increase in lipolytic activity of the hGH 177–191 treated adipose tissues. All these in vivo and in vitro actions on lipid metabolism by the synthetic hGH 177–191 and analogues appear to be the result of the stimulation of the release of the cellular messenger diacylglycerol (FIG. 8) which in turn modulates the key lipolytic enzyme hormone-sensitive lipase (FIG. 9) and lipogenic enzymes acetyl-CoA carboxylase (FIGS. 10A, 10B) in target organs.

Tables 6 and 7 show the in vitro antilipogenic and lipolytic activity of hGH 177–191 and two representative analogues (Ref Nos. 9604 and 9605) on human adipose tissue.

Table 8 shows similar positive lipolytic results on porcine adipose tissue. These results support the expectation that hGH 177–191 and peptide variants thereof shown to be effective in one mammal species will have efficacy in all mammals. Since corresponding sequences of non-human mammals are effectively peptide variants of the human sequence, it is also therefore expected that those corresponding sequences will be effective in other mammals including humans.

Figure 12:
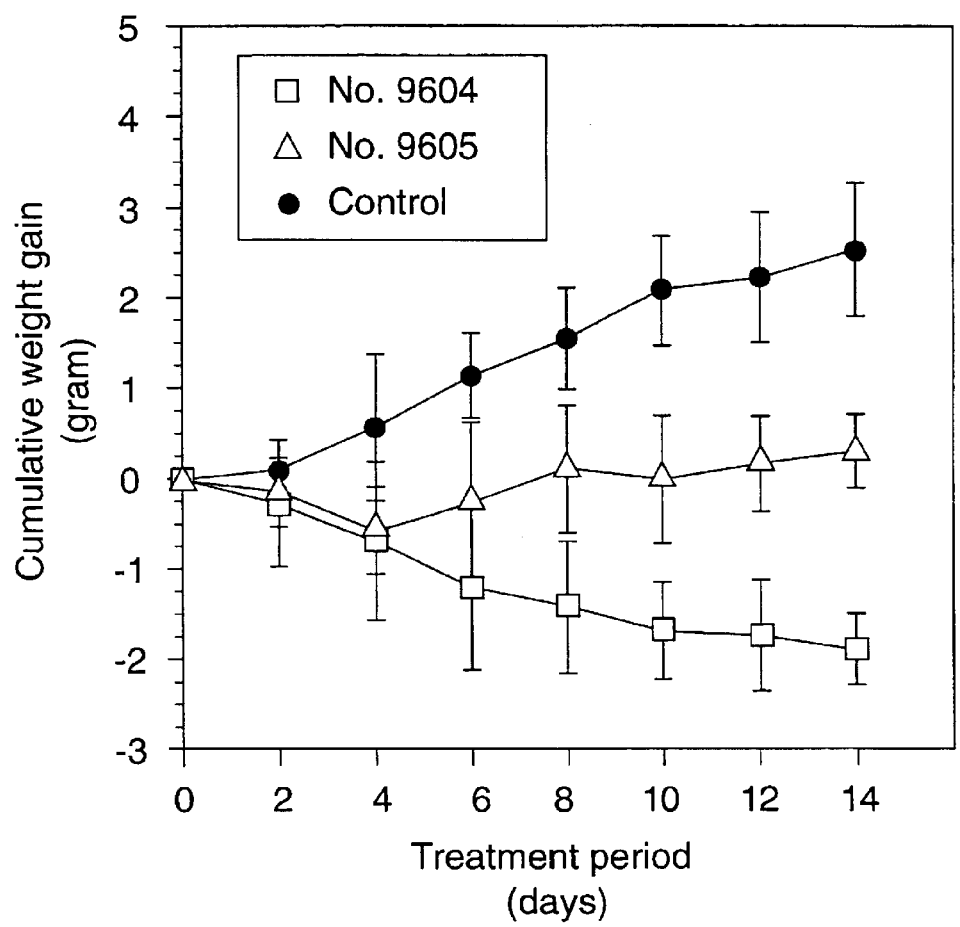
FIG. 12 shows the effect on body weight gain of chronic treatment of 16-week old C57BL/6J(ob/ob) mice with analogues Ref Nos. 9604 (SEQ ID NO: 19) and 9605 (SEQ ID NO: 20).
Figure 13:
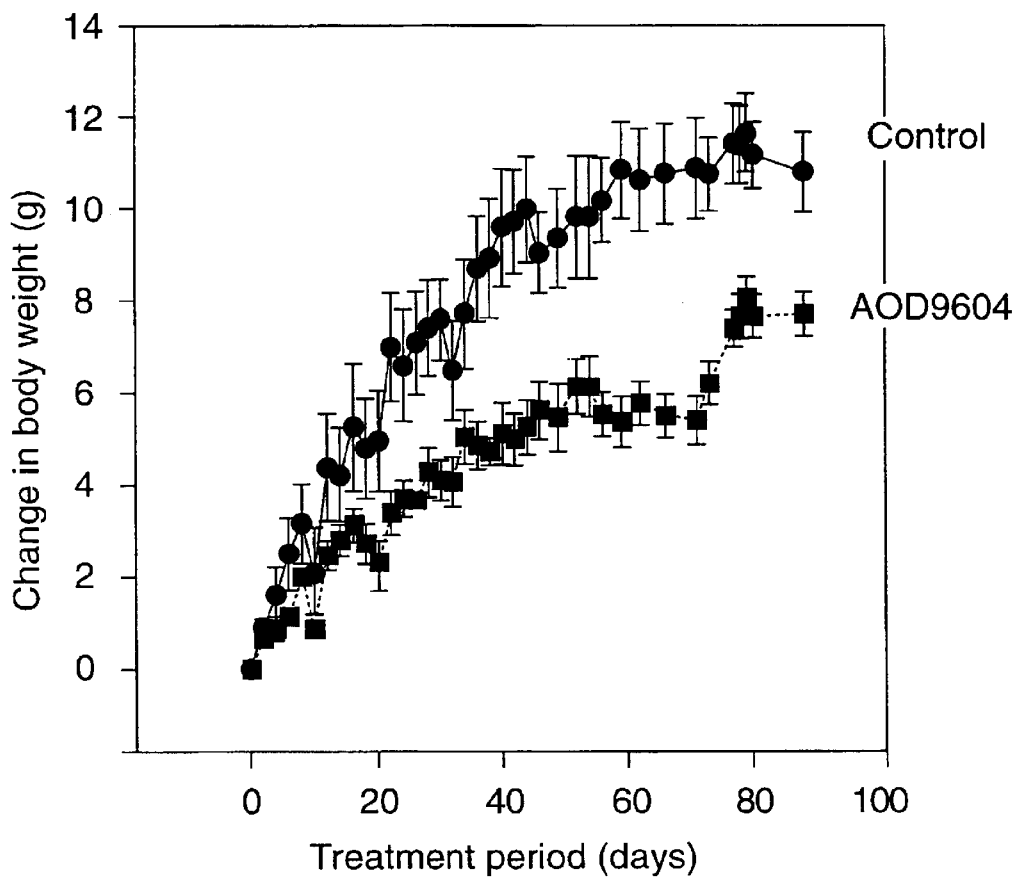
FIG. 13 shows the effect of long-term oral administration of analogue Ref No. 9604 to ob/ob mice.

FIG. 12 shows cumulative weight gain results for analogue Ref No. 9604 and 9605, showing exceptional efficacy of Ref No. 9604 in particular. This in vivo result is consistent with the enhanced in vitro activity of Ref No. 9604 and 9605 compared with hGH 177–191 (Ref No. 9401) shown in Tables 6, 7 and 8. FIG. 13 shows the result of long-term oral administration of analogue Ref No. 9604 at 500 µg/kg daily by oral gavage to ob/ob mice.

The in vivo and in vitro assay results reveal that non-cyclic peptide analogues are generally inactive. (Ref Nos. 9402,9411,9611 and 9617 are non-cyclic). Inactivity also results from alanine substitution at position 178, 183 and 186, with activity being retained for all other alanine substitutions tested (except at 182 and 189 which lead to non cylicity) including one with two d-Alanine substitutions (Ref No. 9501). Ref No. 9606, with Arg replaced by Lys at position 178, also retains activity, as does and Ref No. 9407 with Arg (183) replaced by Lys, and Ref No. 9408 which additionally has an amide bond between Lys (183) and Glu (186).

The inactivity of peptides having analine substitutions at positions 183 and 186 is consistent with the importance of a stabilising salt bridge interaction between opposite charges on Arg (183) and Glu (186) in hGH 177–191. Maintenance of activity with Ref No. 9408 (with an amide bond between Lys (183) and Glu (186)) and with Ref No. 9407 (where Arg (183) is replaced by the similar positively charged Lys(183)) is consistent with the need for a stabilising bond, either covalent or salt-bridge, between position 183 and 186.

TABLE 1

Effect of synthetic hGH 177-191 peptide on body weight and adipose tissue mass of obese mice after 18-day chronic treatment. Animals were given a daily i.p. injection of either hGH 177-191 (200 µg/kg body weight) or equivalent volume of saline as control. All data represent the mean ± SEM of 6 animals (*p < 0.1; **p < 0.05).

| | Male | | Female | |
|---|---|---|---|---|
| Item | Control | Treated | Control | Treated |
| Initial body wt. (g) | 47.5 ± 3.1 | 48.6 ± 2.0 | 46.7 ± 3.6 | 48.2 ± 3.4 |
| Final body wt. (g) | 51.4 ± 3.0 | 51.5 ± 2.3 | 52.1 ± 3.2 | 52.2 ± 2.9 |
| Body wt. gain (g)[a] | 3.9 ± 0.6 | 2.9 ± 0.6* | 5.4 ± 0.4 | 4.0 ± 0.6** |
| Adipose tissue (g)[b] | 3.18 ± 0.43 | 2.52 ± 0.25** | 3.67 ± 0.54 | 3.26 ± 0.25** |

[a] The difference between the initial and final body weights were considered as body weight gain.
[b] The intact epididymal or parametrical fat pads were the representative adipose tissues.

TABLE 2

Effect of synthetic hGH 177-191 on plasma levels of triglyceride and total cholesterol in obese mice after 18-day chronic treatment. Blood samples were collected from the cut tips of the tails of the anaesthetised animals. Data represent the mean ± SEM of 6 animals (*p < 0.05).

| | Male | | Female | |
|---|---|---|---|---|
| Item | Control | Treated | Control | Treated |
| Triglyceride (mmol/l) | 0.63 ± 0.26 | 0.58 ± 0.16 | 0.41 ± 0.19 | 0.38 ± 0.11 |
| Cholesterol (mmol/l) | 4.44 ± 0.56 | 3.52 ± 0.39* | 3.01 ± 0.52 | 2.84 ± 0.29 |

TABLE 3

Female C57BL/6J (ob/ob) mice aged 26 weeks were randomly divided into two groups (Sample number = 6 in each group). The mice were given a daily intraperitoneal (i.p.) injection of analogue Ref No. 9403 (500 µg/kg body weight) or saline for 18 days. After 18 days, all animals were given saline for another 18 days.

| | Treatment (Day 0–18) | | Post-treatment (Day 20–38) | |
|---|---|---|---|---|
| | Drug | | | |
| Item | Ref No: 9403 | Saline | Ref No: 9403 | Saline |
| Initial body weight (g) | 54.74 ± 4.96 | 51.50 ± 2.61 | 54.70 ± 4.15 | 54.08 ± 2.77 |
| Final body weight (g) | 54.42 ± 4.66 | 53.72 ± 2.46 | 56.70 ± 4.45 | 56.14 ± 2.42 |
| Body weight gain (g) | −0.32 ± 0.23 | 2.22 ± 0.22 | 2.00 ± 0.24 | 2.06 ± 0.25 |
| Ave. food consumption (g/mouse/day) | 4.82 ± 0.22 | 4.88 ± 0.29 | 5.03 ± 0.13 | 5.03 ± 0.14 |
| Blood glucose (mM) | 6.2 ± 0.8 | 5.8 ± 0.9 | 6.0 ± 1.0 | 5.7 ± 0.07 |
| Triglyceride (mM) | 0.49 ± 0.10 | 0.60 ± 0.11 | 0.54 ± 0.15 | 0.57 ± 0.08 |

TABLE 4

In vitro effect of peptide analogues on the glycerol release during the lipolysis. Adipose tissues were isolated from male Zucker fatty (fa/fa) rats (12–14 week-old) and incubated with different concentrations of peptide or saline. Each test group contains 6 samples.

| | Glycerol release (µmol/g tissue/hr) | | | |
|---|---|---|---|---|
| Peptide | Analogues | | | |
| concentration (µM) | Ref No. 9401 | Ref No. 9403 | Ref No. 9407 | Ref No. 9404 |
| 0 | 1.42 ± 0.04 | | | |
| 0.1 | 1.82 ± 0.02 | 1.80 ± 0.03 | 1.83 ± 0.11 | 1.75 ± 0.12 |
| 1.0 | 1.86 ± 0.12 | 1.88 ± 0.13 | 1.79 ± 0.07 | 1.94 ± 0.12 |

TABLE 5

In vitro effect of peptide analogues on the inhibition of lipogenesis. Isolated adipose tissues from male Zucker fatty (fa/fa) rats (12–14 week-old) were incubated with peptide (0.3 µM) in KRB buffer containing exogenous insulin (0.1 mU/ml). The rate of [$C^{14}$]-glucose incorporation into [$C^{14}$]-lipid (nmol/g tissue/hr) was measured as the lipogenic activity of adipose tissues. Each test group contains 6 determinations.

| Compound Ref No. (description) | SEQ ID No. | nmol/g tissue/hr | % of control | In vitro lipogenesis Activity |
|---|---|---|---|---|
| Buffer control | — | 243 ± 13 | 100 | =Inactive |
| 9401 (hGH 177–191) | 1 | 161 ± 10 | 75 | Active |
| 9402 (Cys(Acm) at 182 & 189) | 5 | 222 ± 9 | 91 | Inactive |
| 9403 (Lys at 179) | 6 | 167 ± 28 | 69 | Active |
| 9404 (CONH$_2$) | 7 | 187 ± 18 | 77 | Active |
| 9405 (CH$_3$CO) | 8 | 164 ± 17 | 68 | Active |
| 9406 (Ala at 183) | 9 | 236 ± 17 | 97 | Inactive |
| 9407 (Lys at 183) | 10 | 174 ± 16 | 71 | Active |
| 9408 (Lys(183)-Glu(186) amide bond) | 11 | 173 ± 16 | 71 | Active |
| 9410 (desamino) | 12 | 143 ± 20 | 59 | Active |
| 9411 (Cys(SH) at 182 & 189) | 13 | 225 ± 15 | 93 | Inactive |
| 9501 (D-Ala at 187 & 190) | 14 | 185 ± 6 | 76 | Active |
| 9502 (Pen at 182, 189) | 15 | 174 ± 5 | 72 | Active |
| 9601 (Ala at 191) | 16 | 185 ± 24 | 76 | Active |
| 9602 (Ala at 190) | 17 | 176 ± 27 | 73 | Active |
| 9603 (Ala at 178) | 18 | 225 ± 18 | 93 | Inactive |
| 9604 (Tyr elongation) | 19 | 118 ± 16 | 49 | Active |
| 9605 (Lys elongation) | 20 | 184 ± 41 | 76 | Active |
| 9606 (Lys at 178) | 21 | 187 ± 19 | 77 | Active |
| 9607 (Ala at 177) | 22 | 198 ± 12 | 82 | Active |
| 9608 (Ala at 179) | 23 | 173 ± 12 | 71 | Active |
| 9609 (Ala at 180) | 24 | 188 ± 13 | 78 | Active |
| 9610 (Ala at 181) | 25 | 192 ± 14 | 79 | Active |
| 9611 (Ala at 182) | 26 | 224 ± 19 | 93 | Inactive |
| 9612 (Ala at 184) | 27 | 191 ± 20 | 79 | Active |
| 9613 (Ala at 185) | 28 | 189 ± 16 | 78 | Active |
| 9614 (Ala at 186) | 29 | 233 ± 13 | 96 | Inactive |
| 9615 (Ala at 187) | 30 | 183 ± 17 | 76 | Active |
| 9616 (Ala at 188) | 31 | 203 ± 19 | 84 | Active |
| 9617 (Ala at 189) | 32 | 223 ± 16 | 92 | Inactive |
| 9618 (LysLys elongation) | 33 | 188 ± 19 | 77 | Active |

TABLE 6

Antilipogenic activity in Human Abdominal adipose Tissue.

| | $^{14}$C incorporation (Av DPM/mg tissue/hour) |
|---|---|
| Control (BSA + Insulin 0.1 Mu/ml) | 63 ± 5 |
| hGH 177-191 0.1 μM | 40 ± 3 |
| Ref No 9605 0.1 μM | 36 ± 2 |
| Ref No 9604 0.1 μM | 28 ± 3 |

TABLE 7

Lipolytic activity in Human Subcutaneous adipose Tissue

| | Glycerol released (nmol/mg tissue/hour) |
|---|---|
| Control | 480 ± 80 |
| hGH 177-191 0.5 μM | 1000 ± 80 |
| Ref No 9605 0.5 μM | 1100 ± 80 |
| Ref No 9504 0.5 μM | 1200 ± 80 |

TABLE 8

Lipolytic activity in Porcine adipose Tissue.

| | Glycerol released (nmol/mg tissue/hour |
|---|---|
| Control | 300 ± 8 |
| hGH 177-191 0.5 μM | 1300 ± 160 |
| Ref No 9605 0.5 μM | 1350 ± 80 |
| Ref No 9604 0.5 μM | 1600 ± 20 |

REFERENCES

1. Ultsch, M. H., Somers, W., Kossiakof, A. A. and DeVos, A. M. (1994), *J. Mol Biol.* 236: 286–299.
2. Ng, F. M., Bornstein, J., Welker, C., Zimmet, P .Z. and Taft, P. (1974). *Diabetes* 23: 943–949.
3. Frigeri, L. G., Teguh, C., Lind. N., Wolff, G. L. and Lewis, U. J. (1988). *Endocrnology* 122: 2940–2945.
4. Moore, W. V., Moore, K. C., McLachlan, C. G., Fuller, N. J., Burnett, G. B. and Frane, J. W. (1988). *Endocnnology* 122: 2920–2926.
5. Zeisel, H. J., Petrykowski, W. V. and Wais, U. (1992). *Horm. Res.* 37 (Suppl.2): 5–13.
6. Wabitsch, M. and Heinze, E. (1993). *Horm. Res.* 49: 5–9.
7. Christman, G. M. and Halme, J. K. (1992) *Fertil. Sterl.* 57: 12–14.
8. Jacobs, H. S. (1992) *Horn. Res.* 38 (Suppl.1): 14–21.
9. Crist, D. M., Peake, G. T., Loffield, R. B., Kraner, J. C. and Egan, P. A. (1991) *Mech. Ageing Dev.* 58: 191–205.
10. Strobl, J. S. and Thomas, M. J. (1994) *Pharm. Rev.* 46: 1–34.
11. Raben, M. S. and Hollenberg, C. H. (1959) *J. Clin. Invest.* 38: 484–488.
12. Bengtsson, B. A., Eden, S., Lonn, L., Kvist, H., Stokland, A., Lindstedt, G., Bosaeus, I., Tolli, J., Sjostorm, L. and lsaksson, O. G. P. (1993) *J. Clin. Endocninol. Metab.* 76: 309–317.
13. Skaggs, S. R. and Crist, D. M. (1991) *Horm. Res.* 35:19–24.
14. Etherton, T. D., Wiggins, J. P., Evock, C. M., Chung, C. S., Rebhun, J. F., Walton, P. E. and Steele, N. C. (1987). *J. Anim. Sci.* 64: 433–443.
15. Jiang, W. J., Shih, I. L., Tsai, H., Huang, Y. T. and Koh, T. J. (1993). 13th American Peptide Symposium, Edmonton, Canada, P-334 (Abstract).
16. Gertner, J. M. (1993) *Horm. Res.* 40: 10–15.
17. Davidson, M. B. (1987) *Endocrine Rev.* 8: 115–131.
18. Tai, P. K., Liao, J. F., Chen, E. H., Dietz, J., Schwards, J. and Carter-Su, C. (1990) *J. Biol. Chem.* 265; 21828–21834.
19. Dobo, M. (1975) PhD. Thesis, Department of Biochemistry, Monash University, Australia.
20. McNeillie, E. M. and Zammit, V. A. (1982) *Biochem. J.* 204: 273–288.
21. Gertner, J. M. (1992) *Horm. Res.* 38 (Suppl.2): 41–43.
22. Ng, F. M., Adamafio, N. A. and Graystone, J. E. (1990) *J. Mol. Endocrinol.* 4: 43–49.
23. Ng, F. M. and Heng, D. (1988) *Asia Pacific Commun. Biochem.* 2: 47–51.
24. Fossati, P., Prencipe, L. (1982) *Clin. Chem.* 28: 2077–80.
25. Allain, C. C., Poon, L. S., Chan, C. S. G., Richmond, W. and Fu, P. C. Chem. 20: 470–475.
26. Harvey S. et al., "Growth Hormone", CRC Press (1995); Ascacio-Martinez et al. (1994), *Gene*, 143:277–280; Castro-Peretta et al. (1995), *Gene*, 160:311–312.

What is claimed is:

1. peptide of the sequence:

$X^1$m-Leu-Arg-Ile-Val-Gln-Cys-Arg-Ser-Val-Glu-Gly-Ser-Cys-Gly-Phe-$X^2$n(SEQ ID NO:2)

wherein $X^1$ and $X^2$ are each selected from the group consisting of L- or D-Arg, His, Lys and Tyr, and m and n are each 0, 1, 2 or 3 with the proviso that at least m or n is 1;

a cyclic disulfide thereof or an organic or inorganic acid addition salt thereof.

2. A pharmaceutical composition for use in the treatment of obesity in an animal, which comprises an effective amount of a peptide according to claim 1, together with one or more pharmaceutically acceptable carriers and/or diluents.

3. A peptide which is selected from the group consisting of

Lau Arg Ile Val Gln Pen Arg Ser Val Glu Gly Ser Pen Gly Phe (SEQ ID NO: 15),

CH$_3$CO-Leu Arg Ile Val Gln Cys Arg Ser Val Glu Gly Ser Cys Gly Phe (SEQ ID NO: 8),

H—leu Arg Ile Val Gln Cys Arg Ser Val Glu Gly Ser Cys Gly Phe (SEQ ID NO: 12),

Lou Arg Ile Val Gln Cys Arg Ser Val Glu Gly Ser Cys Gly Phe—CONH$_2$ (SEQ ID NO: 7),

Leu Arl Ile Val Gln Cys Lys Ser Val Glu Gly Ser Cys Gly Phe (SEQ ID NO: 10),

Leu Arg Ile Val Gln Cys Lys Ser Val Glu Gly Ser Cys Gly Phe (SEQ ID NO: 11),

Tyr Leu Arg Ile Val Gln Cys Arg Ser Val Glu Gly Ser Cys Gly Phe (SEQ ID NO: 19),

Lys Leu Arg Ile Val Gln Arg Ser Val Glu Gly Ser Cys Gly Phe (SEQ ID NO: 20),

Lys Lys Leu Arg Ile Val Gln Cys Arg Ser Val Glu Gly Ser Cys Gly Phe (SEQ ID NO: 33),

Ala Arg Ile Val Gln Cys Arg Ser Val Glu Gly Ser Cys Gly Phe (SEQ ID NO: 22),

Leu Lys Ile Val Gln Cys Arg Ser Val Glu Gly Ser Cys Gly Phe (SEQ ID NO: 21),

Leu Arg Ala Val Gln Cys Arg Ser Val Glu Gly Ser Cys Gly Phe (SEQ ID NO: 23),

Leu Arg Lys Val Gln Cys Arg Ser Val Glu Gly Ser Cys Gly Phe (SEQ ID NO: 6),

Leu Arg Ile Ala Gln Cys Arg Ser Val Glu Gly Ser Cys Gly Phe (SEQ ID NO: 24),

Leu Arg Ile Val Ala Cys Arg Ser Val Glu Gly Ser Cys Gly Phe (SEQ D NO: 25),

Leu Arg Ile Val Gln Cys Arg Ala Val Gly Ser Cys Gly Phe (SEQ ID NO: 27),

Leu Arg Ile Val Gln Cys Arg Ser Ala Glu Gly Ser Cys Gly Phe (SEQ ID NO: 28),

Leu Arg Ile Val Gln Cys Arg Ser Val Glu Ala Ser Cys Gly Phe (SEQ ID NO: 30),

Leu Arg Ile Val Gln Cys Arg Ser Val Glu Gly Ala Cys Gly Phe (SEQ ID NO: 31),

Leu Arg Ile Val Gln Cys Arg Ser Val Glu Gly Ser Cys Ala Phe (SEQ ID NO: 17),

Leu Arg Ile Val Gln Cys Arg Ser Val Glu D-Ala Ser Cys D-Ala Phe (SEQ ID NO: 14), and Leu Arg Ile Val Gln Cys Arg Ser Val Glu Gly Ser Cys Gly Ala (SEQ ID NO: 16), wherein all amino acids, except for glycine, are of the L-absolute configuration, unless indicated as D-absolute configuration, and the peptide has a cyclic disulfide bond between Cys(182) and Cys(189) or Pen(182) and Pen(189) as appropriate, or an organic or inorganic acid addition salt thereof.

4. A pharmaceutical composition for use in the treatment of obesity in an animal, which comprise an effective amount of a peptide according to claim 3, together with one or more pharmaceutically acceptable carries and/or diluents.

5. A peptide which comprises an analogue of the carboxyl-terminal sequence of a growth hormone, said analog comprising the amino acid sequence:

Tyr-Leu-Arg-Ile-Val-Gln-Cys-Arg-Ser-Val-Glu-Gly-Ser-Cys-Gly-Phe (SEQ ID NO:19)

wherein all amino acids, except for glycine, are of the L-absolute configuration, unless indicated as D-absolute configuration, and the peptide has a cyclic disulfide bond between Cys(182) and Cys(189) or an organic or inorganic acid addition salt thereof.

6. A peptide according to claim 5, sequence: Tyr-Leu-Arg-Ile-Val-Gln-Cys-Arg-Ser-Val-Glu-Gly-Ser-Cys-Gly-Phe (SEQ ID NO:19).

7. A pharmaceutical composition for use in the treatment of obesity in an animal, which comprises an effective amount of a peptide according to claim 6, together with one or more pharmaceutically acceptable carriers and diluents.

8. A pharmaceutical composition for use in the treatment of obesity in an animal, which comprises an effective amount of a peptide according to claim 5, together with one or more pharmaceutically acceptable carriers and diluents.

* * * * *